(12) United States Patent
Ellis et al.

(10) Patent No.: US 9,399,671 B2
(45) Date of Patent: Jul. 26, 2016

(54) METHOD FOR PRODUCING PROTEINS

(75) Inventors: Mark Ellis, Slough (GB); Laura Ellen Newnham, Slough (GB)

(73) Assignee: UCB PHARMA S.A., Brussels (BE)

( * ) Notice: Subject to any disclaimer, the term of this patent is extended or adjusted under 35 U.S.C. 154(b) by 801 days.

(21) Appl. No.: 13/203,182

(22) PCT Filed: Feb. 25, 2010

(86) PCT No.: PCT/EP2010/052413
§ 371 (c)(1),
(2), (4) Date: Oct. 20, 2011

(87) PCT Pub. No.: WO2010/097437
PCT Pub. Date: Sep. 2, 2010

(65) Prior Publication Data
US 2012/0040401 A1    Feb. 16, 2012

(30) Foreign Application Priority Data
Feb. 25, 2009    (GB) .................................. 0903207.9

(51) Int. Cl.
*C12N 15/00* (2006.01)
*C07H 21/04* (2006.01)
*C07K 16/00* (2006.01)

(52) U.S. Cl.
CPC ...................... *C07K 16/00* (2013.01)

(58) Field of Classification Search
None
See application file for complete search history.

(56) References Cited

U.S. PATENT DOCUMENTS

2012/0040401 A1 *  2/2012  Ellis ...................... C07K 16/00
435/69.6

FOREIGN PATENT DOCUMENTS

| WO | 92/02551 A1 | 2/1992 |
|----|-------------|--------|
| WO | 2004/032841 A2 | 4/2004 |
| WO | 2005/042774 A2 | 5/2005 |

OTHER PUBLICATIONS

De Muynck, et al, "Different subcellular localization and glycosylation for a functional antibody expressed in Nicotiana tabacum plants and suspension cells," Transgenic Res (2009) 18:467-482.
Bieri, et al, "Geminivirus sequences as bidirectional transcription termination/polyadenylation signals for economic construction of stably expressed transgenes," Molecular Breeding (2002) 10:107-117.
Babcook, et al, "A novel strategy for generating monoclonal antibodies from single, isolated lymphocytes producing antibodies of defined specificities," 1996, Proc. Natl. Acad. Sci. USA, Immunology, vol. 93, pp. 7843-7848.
Liao, et al, "High-throughput isolation of immunoglobulin genes from single human B cells and expression as monoclonal antibodies," Journal of Virological Methods, 158 (2009) 171-179.

* cited by examiner

*Primary Examiner* — Michael Burkhart
(74) *Attorney, Agent, or Firm* — McDonnell Boehnen Hulbert & Berghoff LLP

(57) ABSTRACT

The invention relates to a transcriptionally active recombinant linear polynucleotide encoding a multimeric protein comprising in the following order, a first promoter sequence, a first encoding polynucleotide sequence, a bidirectional regulatory sequence, a second encoding polynucleotide sequence and a second promoter sequence, wherein the first and second encoding polynucleotide sequences are in convergent transcriptional orientation, each encoding polynucleotide sequence encodes a component of the multimeric protein and the bidirectional regulatory sequence is operably linked to the first and second encoding polynucleotide sequences and the multimeric protein is an antibody or fragment thereof and each encoding polynucleotide sequence encodes one or more antibody domains or fragments thereof.

37 Claims, 6 Drawing Sheets

METHOD FOR PRODUCING PROTEINS

This application is a US national phase of International Application No. PCT/EP2010/052413 filed on Feb. 25, 2010, which claims the benefit of Great Britain patent application 0903207.9, filed Feb. 25, 2009, the disclosures of which are incorporated herein by reference in their entirety.

The present invention relates to a polynucleotide suitable for expressing a multimeric protein, a cell comprising the polynucleotide and a method for preparing the polynucleotide. The invention also relates to a method for producing and expressing a multimeric protein of interest, particularly an antibody or fragment thereof.

Through the use of recombinant DNA, genes that are identified as important, for example in therapeutic applications, can be amplified and isolated. Cells are used extensively to produce a recombinant protein of interest by transfecting the cell with vector comprising the polynucleotide sequence encoding the protein of interest. Cells may be used to produce any desired protein including multimeric proteins, such as antibodies. The use of mammalian cells for expressing recombinant proteins provides a "natural" protein expression pathway wherein the proteins are subjected to the cell's protein folding machinery and further downstream processing. This provides recombinant proteins having the required conformation for in vivo activity.

The continued advancement of mammalian transfection techniques is increasingly important for many applications. This is particularly the case when a large number of proteins of interest are to be expressed and analyzed, such as in high throughput antibody screening projects.

Many research, therapeutic and diagnostic proteins are multimeric proteins comprising a plurality of correctly folded polypeptide chains. The correct functionality of the multimeric protein depends on both the correct protein domain folding of each individual polypeptide chain and their correct association with each other. Antibodies are an example of such a multimeric protein wherein each component polypeptide chain is a fusion protein. IgG antibodies comprise four separate polypeptide chains, two light chains and two heavy chains, wherein each chain is a fusion protein of the variable region and the constant region.

A common method for simultaneous expression of a plurality of proteins employs a plurality of vectors each encoding a desired protein. For example, the production of recombinant antibodies commonly requires the production of the encoding DNA of the desired variable heavy and variable light chains and insertion into plasmid vectors. The plasmid vectors comprise the necessary transcription elements including promoters and terminators for each coding sequence. The vectors may also comprise polynucleotide sequences encoding the constant regions of the heavy and light chains. The vectors are then transfected into host cells. Once transfected into the host cells the vectors may employ the cell's transcription machinery to transcribe the encoding DNA sequence in the vectors, which is transient transfection. Alternatively, the encoding DNA sequence in the vectors may be integrated into the cell's genome, from which the DNA is transcribed, which is stable transfection. The light chain and heavy chain are then expressed by the host cells and various isolation and purification steps are carried out to obtain the final antibody product. There are a number of disadvantages using this method including the difficulty in ensuring that the same number of vectors encoding each antibody chain are transfected into and expressed by the host cells. In addition, the whole process to produce the final antibody product is extremely complex and time consuming requiring multiple digestion and ligation steps.

This method is also necessary for the production of any recombinant multimeric protein comprising two or more component polypeptide chains which assemble to form the functional multimeric protein.

It is also known in the art to express multiple proteins from one vector using internal ribosome entry sites (IRES), which allow translation initiation in the middle of a mRNA sequence. This method also has disadvantages because the gene sequence positioned downstream of the IRES sequence is likely to provide a lower expression level compared to the gene sequence positioned upstream of the IRES sequence.

WO 2005/042774 discloses a multiplex overlap-extension PCR method to link two or more nucleotide sequences encoding for domains or components of a heteromeric protein in a single reaction. This document discloses that the method may be used to link a cognate pair of non-contiguous nucleic acids of interest that are contained within or derived from a single cell. The method is disclosed as particularly useful for linking antibody heavy chain variable region and antibody light chain variable region encoding sequences from a single cell. The cognate pair may comprise one or more constant region encoding sequences in addition to the variable region encoding sequences. However, the resulting nucleotide product from the method still requires cloning and insertion into an appropriate expression vector to allow expression in a suitable host cell.

Accordingly, there is a need to provide improved methods for producing recombinant multimeric proteins which overcome the disadvantages of methods currently used in the art.

SUMMARY OF INVENTION

It is an aim of the present invention to solve one or more of the problems described above. According to a first aspect of the present invention there is provided a transcriptionally active recombinant linear polynucleotide encoding a multimeric protein comprising in the following order, a first promoter sequence, a first encoding polynucleotide sequence, a bidirectional regulatory sequence, a second encoding polynucleotide sequence and a second promoter sequence, wherein the first and second encoding polynucleotide sequences are in convergent transcriptional orientation, each encoding polynucleotide sequence encodes a component of the multimeric protein and the bidirectional regulatory sequence is operably linked to the first and second encoding polynucleotide sequences and the multimeric protein is an antibody or fragment thereof and each encoding polynucleotide sequence encodes one or more antibody domains or fragments thereof.

In a second aspect of the present invention there is provided a cell comprising a transcriptionally active recombinant linear polynucleotide as defined above.

In a third aspect of the present invention there is provided an expression system comprising a polynucleotide as defined above and a solvent or medium.

In a fourth aspect of the present invention there is provided a method of producing a transcriptionally active recombinant linear polynucleotide encoding a multimeric protein comprising in the following order, a first promoter sequence, a first encoding polynucleotide sequence, a bidirectional regulatory sequence, a second encoding polynucleotide sequence and a second promoter sequence, wherein the first and second encoding polynucleotide sequences are in convergent transcriptional orientation, each encoding polynucleotide sequence encodes a component of the multimeric protein, the bidirectional regulatory sequence is operably linked to the first and second encoding polynucleotide sequences, and the multimeric protein is an antibody or fragment thereof and each component of the multimeric protein is one or more antibody domains or fragments thereof, wherein the method comprises:

a) providing the first and second promoter sequences, the first encoding polynucleotide sequence comprising the whole or a part of a first multimeric component encoding polynucleotide sequence; the second encoding polynucleotide sequence comprising the whole or a part of a second multimeric component encoding polynucleotide sequence; and a third polynucleotide sequence comprising the bidirectional regulatory sequence and optionally comprising a part of the first and/or second multimeric component encoding polynucleotide sequences;

b) fusing the first encoding polynucleotide sequence to the third polynucleotide sequence;

c) fusing the second encoding polynucleotide sequence to the third polynucleotide sequence; and d) fusing the first promoter sequence to the first encoding polynucleotide sequence and fusing the second promoter sequence to the second encoding polynucleotide sequence.

The present invention also provides a method for obtaining a recombinant antibody with a desired function, comprising:

a) providing a population of antibody-forming cells suspected of containing at least one cell capable of producing an antibody exhibiting the desired function;

b) generating a transcriptionally active recombinant linear polynucleotide from the antibody forming cells obtained in step (a) wherein the transcriptionally active recombinant linear polynucleotide comprises in the following order:
  (i) a first promoter sequence;
  (ii) a first encoding polynucleotide sequence encoding one or more antibody variable domains or fragments thereof of an antibody produced by an antibody-forming cell obtained in step (a);
  (iii) a bidirectional regulatory sequence
  (iv) a second encoding polynucleotide sequence encoding one or more antibody variable domains or fragments thereof of an antibody produced by an antibody-forming cell obtained in step (a); and
  (v) a second promoter sequence,
wherein the first and second encoding polynucleotide sequences are in convergent transcriptional orientation, each encoding polynucleotide sequence encodes a component of an antibody and the bidirectional regulatory sequence is operably linked to the first and second encoding polynucleotide sequences;

c) expressing a recombinant antibody using the transcriptionally active recombinant linear polynucleotide generated in step (b);

d) screening the recombinant antibody produced by step (c) for the desired function; and e) optionally repeating steps (b), (c) and (d) to identify a recombinant antibody exhibiting the desired function.

In a fifth aspect of the present invention there is provided a method of expressing a multimeric protein, comprising:

a) transfecting a cell with the transcriptionally active recombinant linear polynucleotide as defined above; and b) expressing the multimeric protein encoded by the transcriptionally active recombinant linear polynucleotide.

The transcriptionally active recombinant linear polynucleotide, the cell, expression system and the methods provided by the present invention are advantageous because they provide a more efficient, simplified and quicker way to produce a multimeric protein, particularly antibodies. The transcriptionally active recombinant linear polynucleotide, cell, expression system, and the methods avoid the need for multiple digestion and ligation steps to produce vectors, multiple transformations into host cells, and allow a faster and easier way to obtain the final recombinant multimeric protein.

The cell according to the present invention may also be capable of being transfected with a greater number of exogenous linear transcriptionally active polynucleotides compared to the same number of plasmids. Accordingly, the cell and the method of the present invention may provide a more efficient transfection and expression method and may provide a higher yield of expressed multimeric protein compared to the use of plasmids.

In a sixth aspect the present invention also provides the use of a bidirectional regulatory sequence for expressing two protein encoding polynucleotide sequences, wherein each encoding polynucleotide sequence encodes a component of a multimeric protein.

BRIEF DESCRIPTION OF THE DRAWINGS

In the following drawings specific embodiments of the present invention are described by way of example only, in which.

BRIEF SUMMARY OF THE SEQUENCES

Figure 1:
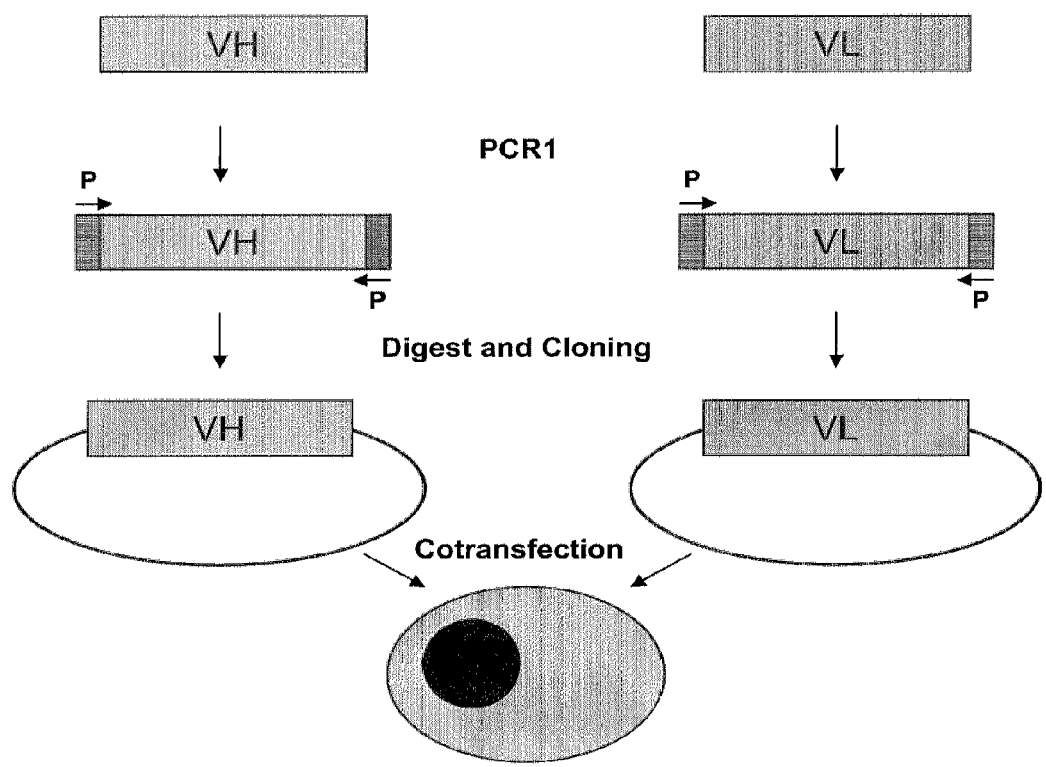
FIG. 1 is a schematic diagram of a known standard method used to clone and express antibody variable regions using expression vectors wherein the variable heavy chain (VH) and variable light chain (VL) encoding sequences are amplified by PCR in the presence of primers (P) which add restrictions sites at the 5' and 3' ends of the VH and VL sequences which are shown as shaded regions either side of the VH and VL sequences; the restriction sites allow downstream digestion and ligation into separate expression vectors which may comprise downstream constant domain sequences; the two expression vectors are then transfected into a cell to provide a transient or stably transfected cell capable of expressing the desired antibody.

SEQ ID NO: 1 is the nucleotide sequence of a forward primer comprising a region complementary to 5' end of a sequence comprising a polyA sequence and an overlap-extension tail comprising an EcoRI site.

SEQ ID NO: 2 is the nucleotide sequence of a reverse primer comprising a region complementary to the 3' end of a sequence comprising a polyA sequence and an overlap-extension tail comprising an EcoRI site.

SEQ ID NO: 3 is the nucleotide sequence of a primer comprising a region complementary to the 5' end of a variable light chain domain containing sequence and an overlap-extension tail complementary to the 3' end of a first CMV promoter sequence.

SEQ ID NO: 4 is the nucleotide sequence of a primer comprising a region complementary to the 3' end of a variable light chain domain sequence and an overlap-extension tail complementary to the 5' end of a constant light chain domain sequence.

SEQ ID NO: 5 is the nucleotide sequence of a primer comprising a region complementary to the 5' end of a variable heavy chain domain containing sequence and an overlap-extension tail complementary to the 3' end of a second SFFV promoter sequence.

SEQ ID NO: 6 is the nucleotide sequence of a primer comprising a region complementary to the 3' end of a variable heavy chain domain sequence and an overlap-extension tail complementary to the 5' end of a constant heavy chain domain sequence.

SEQ ID NO: 7 is the nucleotide sequence of a primer which is complementary to a non-coding region at the 5' end of the first CMV promoter sequence.

SEQ ID NO: 8 is the nucleotide sequence of a primer which is complementary to a non-coding region at the 5' end of the second SFFV promoter sequence.

SEQ ID NO: 9 is the nucleotide sequence comprising in the following order, a constant light (kappa) domain coding sequence, bidirectional polyA sequence and a constant heavy domain coding sequence, wherein the constant light domain coding sequence and constant heavy domain coding sequence are in convergent transcriptional orientation.

SEQ ID NO: 10 is the nucleotide sequence comprising the sequence of the first CMV promoter (F1 L).

SEQ ID NO: 11 is the nucleotide sequence comprising the sequence of the second SFFV promoter (F1 H).

DETAILED DESCRIPTION OF THE INVENTION

The present invention will now be described in more detail.
The terms "protein" and "polypeptide" are used interchangeably herein, unless the context indicates otherwise. "Peptide" is intended to refer to 10 or less amino acids.

The terms "polynucleotide" includes a gene, DNA, cDNA, RNA, mRNA etc unless the context indicates otherwise. The polynucleotide may be double or single stranded.

As used herein, the term "comprising" in context of the present specification should be interpreted as "including".

The term "distinct" in the context of the present invention means that the polynucleotides are different/non-identical. The polynucleotides may, for example, have 95% or less homology, 90% or less homology, 85% or less homology, 80% or less homology or 75% or less homology when the full length sequences are compared, for example, using suitable software such as BLAST.

The term "exogenous" in the context of the present invention means that polynucleotide sequences originated from outside the host cell.

The term "multimeric protein" in the context of the present invention means a protein complex comprising a plurality, such as 2 or 3, component protein chains where the component chains associate with each other by covalent or non-covalent bonds to form the multimeric protein. The multimeric protein is an antibody.

The term "fusion protein" in the context of the present invention means a polypeptide comprising a plurality of subunits wherein each subunit is encoded by a separate encoding polynucleotide sequence. Each encoding polynucleotide sequence comprises one or more gene sequences or fragments thereof. Translation of the plurality of subunit encoding polynucleotide sequences results in a single polypeptide chain. The subunits of the fusion protein may be linked directly in the polypeptide chain or linked via a suitable linker sequence. Typically the fusion protein is a heavy chain or light chain of an antibody comprising a variable domain and a constant domain or fragments thereof.

The term "transcriptionally active recombinant linear polynucleotide" in the context of the present invention is a linear polynucleotide comprising the necessary elements required for transcription of the encoding sequences in the polynucleotide after transfection into the host cell. The linear transcriptionally active polynucleotide comprises two promoter sequences and a bidirectional regulatory sequence. The bidirectional regulatory sequence is typically a sequence capable of forming the end of the RNA transcript for each encoding polynucleotide sequence. The bidirectional regulatory sequence may form the end of each RNA transcript by terminating transcription and/or cleaving each RNA transcript.

Traditionally, polynucleotides are handled in the form of plasmids. This may be because the plasmid provides a relatively stable form in which the relevant polynucleotide can be handled, stored, manipulated and the like. Plasmid DNA is not linear transcriptionally active polynucleotide within the context of the present specification, but may be cleaved to provide linear transcriptionally active polynucleotide. In one embodiment the linear transcriptionally active polynucleotide does not comprise backbone vector sequences. In one embodiment the transcriptionally active polynucleotide is not capable of autonomous replication, for example the transcriptionally active polynucleotide does not comprise an origin of replication.

Each linear transcriptionally active polynucleotide may be in the form of a transcriptionally active DNA fragment as described in U.S. Pat. No. 6,280,977 and Liang, X et al, 2002, The Journal of Biological Chemistry, 227(5), 3593-3598, which disclose transcriptionally active PCR (TAP) fragments used for expression experiments.

Whilst U.S. Pat. No. 6,280,977 and Liang, X et al, 2002, The Journal of Biological Chemistry, 227(5), 3593-3598 disclose a method for producing a linear transcriptionally active polynucleotide and the use of a linear transcriptionally active polynucleotide for expressing a protein, it is not described or suggested that each linear transcriptionally active polynucleotides may comprise two converging encoding polynucleotide sequences wherein each encoding polynucleotide sequence encodes a component of a multimeric protein, such as a heavy chain or light chain of an antibody or a fragment thereof, and a bidirectional regulatory sequence.

The term "operably linked" in the context of the present invention refers to an arrangement of sequences wherein the sequences are configured so as to perform their desired function.

The linear transcriptionally active polynucleotide comprises a bidirectional regulatory sequence positioned between two encoding polynucleotide sequences and a promoter sequence is positioned upstream of each encoding polynucleotide sequence.

The linear transcriptionally active polynucleotide may be any suitable nucleic acid sequence such as DNA or RNA.

The component sequences of the polynucleotide including the promoters and bidirectional regulatory sequence and the protein coding sequences may be separated by non-coding/non-functional nucleotide sequences.

Each protein encoding sequence may comprise one or more non-coding sequences such as introns, which may be removed by splicing of the mRNA.

In one embodiment the component polynucleotide sequences are not separated by non-coding sequences, such as introns, and are contiguously linked.

Figure 2:
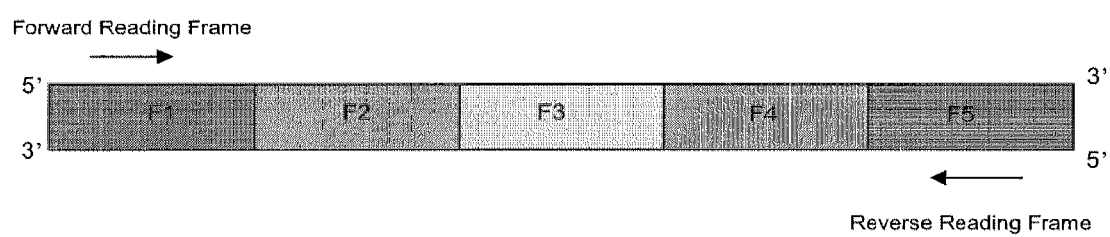
FIG. 2 is schematic diagram of an example transcriptionally active polynucleotide sequence provided by the present invention wherein F1 is a first promoter sequence, F2 is a first encoding polynucleotide sequence, F3, is a third polynucleotide sequence comprising a bidirectional regulatory sequence, F4 is a second encoding polynucleotide sequence and F5 is a second promoter sequence.

The first and second encoding polynucleotide sequences are in convergent transcriptional orientation which means that the coding strands are in opposite direction with respect to the direction of transcription by RNA polymerase. The first and second promoter sequences are also orientated in opposite directions. As shown in FIG. 2, the forward reading frame from the first promoter (F1) causes RNA polymerase to bind to the 5' end of the top DNA strand (forward reading frame) and transcribe the coding strand of the first encoding polynucleotide sequence (top DNA strand of F2) and the reverse reading frame from the second promoter (F5) causes RNA polymerase to bind to the reverse reading frame (bottom DNA strand) and transcribe the coding strand of the second encoding polynucleotide sequence (bottom DNA strand of F4).

Any suitable encoding polynucleotide sequences may be employed in the linear transcriptionally active polynucleotide. The encoding sequences may be the minimum sequence encoding a component of a multimeric protein of interest i.e. which consists essentially of the nucleotide sequences encoding the relevant polypeptide. Each encoding polynucleotide sequence encodes one or more genes or fragments thereof.

Each encoding polynucleotide sequence may be identical to an endogenous polynucleotide sequence encoding a protein or a mutated version thereof, for example with attenuated biological activity, or fragment thereof. Alternatively, each encoding sequence employed in the present invention encodes a heterologous protein, not normally expressed by the host cell.

In one embodiment each encoding polynucleotide sequence is autologous. Alternatively each encoding polynucleotide sequence may be heterologous.

The linear transcriptionally active polynucleotide may comprise a plurality of identical encoding polynucleotide sequences and/or a plurality of distinct encoding polynucleotide sequences.

The encoding polynucleotide sequences may encode a multimeric protein of interest which may be any suitable multimeric protein including therapeutic, prophylactic or diagnostic proteins.

The one or more proteins expressed may also contain a tag or label to assist in purification/separation.

The linear transcriptionally active polynucleotide may comprise one or more further encoding polynucleotides sequences for expression which form one or more separate polypeptide chains after translation. In one embodiment the linear transcriptionally active polynucleotide comprises a plurality of further encoding polynucleotides, wherein each encoding polynucleotide sequence encodes a further component of the same or a different multimeric protein.

The cell according to the present invention may also comprise one or more further distinct linear transcriptionally active polynucleotides, wherein each further linear transcriptionally active polynucleotide comprises an encoding polynucleotide sequence, preferably a plurality of encoding polynucleotide sequences each encoding a component of a multimeric protein as defined above. Preferably the cell comprises a plurality of linear transcriptionally active polynucleotides, wherein each polynucleotide comprises distinct plurality of encoding polynucleotide sequences encoding distinct multimeric proteins for expression preferably in the form of polynucleotide as defined above.

The encoding polynucleotide sequences each encode a component of a multimeric protein. Each component of the multimeric protein may associate to form the multimeric protein by any suitable means, for example by covalent and/or non-covalent bonds.

The multimeric protein may be formed from a plurality of identical and/or distinct proteins expressed by the transcriptionally active linear polynucleotide according to the present invention.

The transcriptionally active linear polynucleotide may encode protein components of a multimeric protein which form a cognate pair derived from a single cell. Accordingly, expression of the proteins from the transcriptionally active polynucleotide in the cell ensures that the original activity of the multimeric protein is maintained.

The component protein sequences preferably co-assemble in the cell according to the present invention after expression. Accordingly, a further advantage of the present invention is that the multimeric protein produced is assembled in the cell and may have the desired conformation required for in vivo activity.

In one embodiment, one or both of the encoding polynucleotide sequences encodes a fusion protein comprising a plurality of subunits.

In the embodiment wherein one or both of the encoding polynucleotide sequences encodes a fusion protein comprising a plurality of subunits, each subunit encoding sequences may be separated by one or more non-coding sequences such as introns, which may be removed by splicing of the mRNA. In one embodiment the coding polynucleotide sequences are separated by a linker sequence, which preferably encodes a polypeptide linker. The polypeptide linker may be any suitable length in order to allow the subunits of the fusion protein to assemble into a functional fusion protein.

In one embodiment the fusion subunit coding polynucleotide sequences are not separated by non-coding sequences or linker sequences and are contiguously linked.

Each encoding polynucleotide sequence may comprise any suitable number of fusion protein subunit encoding polynucleotide sequences which together form a fusion protein. Preferably each encoding polynucleotide sequence comprises 2 fusion protein subunit encoding polynucleotide sequences, 3 fusion protein subunit encoding polynucleotide sequences or 4 fusion protein subunit encoding polynucleotide sequences.

The multimeric protein is an antibody or fragment thereof and each encoding polynucleotide sequence encodes one or more antibody domains or fragments thereof.

Antibodies in the context of the present invention include whole antibodies of any suitable class for example, IgA, IgD, IgE, IgG or IgM or subclass such as IgG1, IgG2, IgG3 or IgG4 and functionally active fragments or derivatives thereof and may be, but are not limited to, monoclonal, humanized, fully human or chimeric antibodies. Antibodies may therefore comprise a complete antibody molecule having full length heavy and light chains or a fragment thereof and may be, but are not limited to VH, VL, VHH, Fab, modified Fab, Fab', F(ab')$_2$, Fv, bi, tri or tetra-valent antibodies, scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews-Online 2(3), 209-217). Other antibody fragments include the Fab and Fab' fragments described in International patent applications WO2005/003169, WO2005/003170 and WO2005/003171. Multi-valent antibodies may comprise multiple specificities or may be monospecific (see for example WO 92/22853 and WO05/113605).

The constant domains of the antibody molecule, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required, e.g. for simply blocking activity. It will be appreciated that sequence variants of these constant region domains may also be used.

Accordingly, in one embodiment of the present invention each encoding polynucleotide sequence encodes one or more antibody domains or fragments thereof "Antibody domain" in the context of the present invention means a variable or constant domain or fragment thereof of an antibody. The term "region" may be used interchangeably with the term "domain". Examples of antibody domains include VH, VL, VHH, IgNAR variable domains, CL, CH1, CH2 and CH3 constant domains.

Reference to "the constant heavy chain domain" or "one or more constant heavy chain domains" may refer to one or more domains of CH1, CH2 and CH3. Any selected encoding polynucleotide sequence may comprise a whole antibody domain, comprise a fragment of an antibody domain or comprise two or more antibody domains or fragments thereof.

The expressed proteins preferably assemble into a multimeric antibody protein comprising a plurality of identical and/or distinct proteins.

Any combination of one or more domains or fragments thereof may be encoded by each encoding polynucleotide sequence.

In the above examples of antibody formats which may be single polypeptide chain antibody format including VH, VL, VHH, IgNAR, scFv, the present invention also provides a transcriptionally active recombinant linear polynucleotide encoding two single polypeptide chain antibodies, comprising in the following order, a first promoter sequence, a first encoding polynucleotide sequence, a bidirectional regulatory sequence, a second encoding polynucleotide sequence and a second promoter sequence, wherein the first and second encoding polynucleotide sequences are in convergent transcriptional orientation, and the bidirectional regulatory sequence is operably linked to the first and second encoding polynucleotide sequences and each encoding polynucleotide sequence encodes a single polypeptide chain antibody or fragment thereof selected from VH, VL, VHH, scFv. The selected variable domains in each encoding polynucleotide sequence may be the same or different domains. The expressed variable domains may be separate and not associate to form a multimeric protein. Alternatively, the variable domains may associate to form a multimeric protein such as VH-VH, VL-VL, VH-VL or VH-VL. The components of the multimeric protein may associate by covalent or non-covalent means.

In one embodiment one encoding polynucleotide sequence encodes a light chain of an antibody or a fragment thereof. In this embodiment the light chain or fragment thereof preferably is encoded by a variable domain encoding polynucleotide sequence and a constant domain containing polynucleotide sequence.

In a further embodiment one encoding polynucleotide sequence encodes a heavy chain of an antibody or a fragment thereof. In this embodiment the heavy chain or fragment thereof preferably is encoded by a variable domain encoding polynucleotide sequence and a constant domain containing polynucleotide sequence.

In a preferred embodiment, the first encoding polynucleotide sequence encodes a light chain of an antibody or a fragment thereof and the second encoding polynucleotide sequence encodes a heavy chain of an antibody or a fragment thereof. The light chain and heavy chain polypeptide sequences encoded by the transcriptionally active polynucleotide preferably assemble in the cell to form the multimeric antibody or a fragment thereof after expression e.g. a Fab or Fab' fragment.

Each antibody domain may be derived from the same or different source. Accordingly, in the embodiment wherein the linear transcriptionally active polynucleotide encodes a variable domain and one or more constant domains from a light chain and/or heavy chain, the variable domains and constant domains may be heterologous. For example, the variable domains, or fragments thereof, may be derived from a mouse and the constant domains may be human.

In one embodiment the variable heavy chain sequence and variable light chain sequence may form a cognate pair from a single cell, thereby maintaining the binding affinity of the endogenous antibody from the cell. In a further embodiment, the variable heavy chain sequence and the variable light chain sequence do not form a cognate pair. In this embodiment the variable heavy chain sequences and variable light chain sequences may be randomly paired sequences derived from a population of genetically diverse cells.

After expression of the antibody or fragment thereof may be further processed, for example by conjugation to another entity or for example PEGylated to generate a product with the required properties.

In one aspect the antibody or fragment thereof produced is useful in therapy or diagnosis, research, analysis, assays or the like. The antibodies of the present disclosure may possess various modifications. For example, the antibodies may be conjugated to one or more reporter or effector molecules, tags or labels such a radiolabel, luminescent/fluorescent label, for any suitable diagnostic or therapeutic purpose.

The linear transcriptionally active polynucleotide of the present invention comprises a first promoter sequence, a second promoter sequence and a bidirectional regulatory sequence.

As used herein, the term "promoter" is a DNA sequence which generally extends upstream from the transcription initiation site and is involved in binding of RNA polymerase. The promoter may contain several short (<10 base pair) sequence elements that bind transcription factors, generally dispersed over >200 base pairs. A promoter that contains only elements recognized by general and upstream factors is usually transcribed in any cell type. Such promoters may be responsible for expression of cellular genes that are constitutively expressed (sometimes called housekeeping genes). There are also tissue-specific promoters limited to particular cell types, such as the human metallothionein (MT) promoter which is upregulated by heavy metal ions and glucocorticoids. Any suitable promoter sequence may be employed in the present invention depending on the type of host cell employed. Examples of suitable promoters include CMV such as hCMV, lac (a bacterial cell promoter), viral LTR promoters, SFFV promoter, SV40 promoter, elongation factor promoter (EFA1) and immediate early promoter IE1 for insect host cells. Any other baculovirus promoters that are expressed independent of the baculovirus gene expression could also be used such as for example the gp64 promoter. One or more promoters employed may be inducible promoters.

The promoters in the linear transcriptionally active polynucleotide may be the same or different. If the promoters are different, the strength of the promoters may be advantageously selected in order to selectively up-regulate or down-regulate the expression of one encoding polynucleotide compared to the other encoding polynucleotide.

The linear transcriptionally active polynucleotide may comprise an enhancer sequence upstream of the promoter sequence. For example, a homologous region 5 (hr5) enhancer sequence may be positioned upstream of an immediate early promoter (IE1) promoter sequence for insect host cells.

The linear transcriptionally active polynucleotide comprises a bidirectional regulatory sequence. The bidirectional regulatory sequence is any suitable transcription regulatory DNA sequence that is capable of forming the end of each RNA, including mRNA or pre-mRNA, transcript formed from the encoding polynucleotide sequences. The bidirectional regulatory sequence may form the end of each RNA transcript by terminating transcription and/or initiating cleavage of the RNA transcript during or after transcription.

In the embodiment wherein the bidirectional regulatory sequence is a transcription terminator, the sequence typically causes the RNA polymerase to cease transcription by forming a stem-loop structure in the RNA. The stem-loop structure causes the RNA polymerase to fall away from the DNA, therefore, terminating transcription.

In the embodiment wherein the bidirectional regulatory sequence initiates cleavage of the RNA transcript, the sequence in the RNA transcript causes one or more proteins to bind the RNA transcript and cleave it, thereby forming the end of the RNA transcript. A suitable sequence is a polyadenylation sequence which is transcribed in the RNA where it causes an enzyme to bind and catalyze cleavage of the RNA and also causes an enzyme to add A residues at the 3' end, thereby forming a polyadenylation tail. The polyadenylation sequence may protect the mRNA from exonucleases thereby stabilizing mRNA production. Examples of polyadenylation sequences include SV40poly A, or poly A sequences derived from other viruses, for example Mastreviruses, and synthetic polyA sequence.

One example of a polyadenylation sequence is SV40polyA sequence which comprises a stretch of 6 nucleotides TTATTT which becomes AAUAAA on the pre-mRNA and attracts an enzyme called CPSF (cleavage/polyadenylation specificity factor). This enzyme binds to AAUAAA (or versions similar to this sequence) and begins the complex process of mRNA cleavage (about 10 to 30 base pairs downstream) and polyadenylation. This process includes attracting a number of proteins to form a complex. This protein complex cleaves the mRNA and an enzyme called polyadenylate polymerase adds A residues to form the polyadenylation tail.

Bidirectional termination or polyadenylation sequences are known in the art to allow transcription of converging sequences. Bieri, S et al, 2002, Molecular Breeding, "Geminivirus sequences as bidirectional transcription termination/polyadenylation signals for economic construction of stably expressed transgenes", 10; 107-117 discloses the testing of geminivirus terminator sequences from three different viruses for their potential to allow efficient gene expression in transfected rice protoplasts. The wheat dwarf virus terminator was used to express two convergent genes, GUS and LUC. Whilst bidirectional regulatory sequences such as bidirectional polyA sequences as used in viruses are known to exist they are not known to have use in the expression of proteins of interest, such as antibodies, and have not been used in a transcriptionally active polynucleotide sequence encoding a multimeric protein according to the present invention.

In one embodiment the bidirectional regulatory sequence terminates transcription and initiates cleavage of the RNA transcript. For example, it is thought that the SV40polyA sequence is capable of initiating cleavage of the RNA transcript and also terminating transcription by RNA polymerase, thereby ensuring that unnecessary transcription continues after the bidirectional regulatory sequence of the forward and reverse reading frame.

In one embodiment the linear transcriptionally active polynucleotide comprises a bidirectional transcription terminator. In this embodiment the linear transcriptionally active polynucleotide may further comprise a polyadenylation sequence positioned on both sides of the bidirectional terminator sequence.

In an alternative embodiment the transcriptionally active linear polynucleotide only comprises one bidirectional regulatory sequence, such as a bidirectional polyadenylation sequence. Accordingly, in this embodiment, polynucleotide sequence comprising two or more regulatory sequences, such as transcription terminators or polyadenylation sequences, are excluded from the scope of the present invention.

The bidirectional regulatory sequence is operably linked to the first and second encoding polynucleotide sequences which means that the bidirectional regulatory sequence capable of forming the end of the RNA transcript for both the first and second encoding polynucleotide sequences which are in convergent transcriptional orientation and positioned either side of the bidirectional regulatory sequence, as shown in FIG. 2.

In one embodiment there is provided a transcriptionally active recombinant linear polynucleotide encoding a multimeric protein consisting of two converging encoding polynucleotide sequences, a bidirectional regulatory sequence positioned between the two encoding polynucleotide sequences and a promoter sequence positioned upstream of each encoding polynucleotide sequence, wherein each encoding polynucleotide sequence encodes a component of the multimeric protein.

The linear transcriptionally active polynucleotide may comprise one or more introns. In one embodiment one or more of the polynucleotide sequences comprise one or more introns within each encoding polynucleotide sequence and/or between each encoding polynucleotide sequence.

In one embodiment each encoding polynucleotide sequence comprises 1, 2 or 3 introns.

The intron may be derived from any gene, particularly a gene from which the encoded sequence is derived.

In one embodiment the linear transcriptionally active polynucleotide does not comprise an intron between the first promoter and the first encoding polynucleotide sequence and does not comprise an intron between the second promoter and the second encoding polynucleotide sequence. In one embodiment the linear transcriptionally active polynucleotide does not comprise any introns.

In one embodiment the linear transcriptionally active polynucleotide comprises a Kozak sequence, for example the natural sequence associated with sequence encoding the desired polypeptide. Whilst not wishing to be bound by theory, it is thought that a Kozak sequence in the mRNA, may have a role to play in assembling the ribosome for translation of the mRNA.

In one embodiment the linear transcriptionally active polynucleotide sequence does not comprise an internal ribosome entry site (IRES) sequence which allows translation initiation in the middle of mRNA. The use of one or more IRES sequences in the linear transcriptionally active polynucleotide sequences is not required because separate promoters initiate transcription for each encoding polynucleotide sequence, which are converging.

The ends of linear transcriptionally active polynucleotide may comprise peptide nucleic acid (PNA) tails, claims and/or "clamp tails" to protect the ends of the polynucleotide from digestion by exonucleases after the polynucleotides have been transfected into a cell. Suitable PNAs are described in U.S. Pat. No. 6,280,977. Alternatively, in one embodiment the linear transcriptionally active polynucleotide does not comprise or is not attached to a PNA including a PNA tail, PNA clamp, PNA "claim tail" or PNA molecule.

In one embodiment, one or more of the first promoter sequence, first encoding polynucleotide sequence, bidirectional regulatory sequence, second encoding polynucleotide sequence and second promoter sequence comprises on one or both sides a restriction site. In one embodiment each end of the linear transcriptionally active polynucleotide comprises a restriction site suitable for cloning the polynucleotide into a vector.

The present invention also provides a vector comprising the transcriptionally active recombinant polynucleotide as defined above. The transcriptionally active recombinant polynucleotide may be directly cloned into any suitable vector by any suitable method.

In an alternative embodiment the linear transcriptionally active polynucleotide is not suitable for cloning into a vector for example, each end of the linear transcriptionally active polynucleotide does not comprise a restriction site.

The present invention also provides the use of a bidirectional regulatory sequence for expressing two protein encoding polynucleotide sequences, wherein each encoding polynucleotide sequence encodes a component of a multimeric protein. The bidirectional regulatory sequence, the encoding polynucleotide sequences and transcriptionally active linear polynucleotide sequence which may be employed in the use are as defined above.

The present invention also provides a cell comprising one or more transcriptionally active recombinant linear polynucleotides as defined above.

Any cell able to express the fusion protein encoded by the linear transcriptionally active polynucleotide may be employed in the present invention. Suitable cells for employing in the invention include eukaryotic cells, for example plant cells, insect cells such as *Spodoptera frugiperda* Sf9, *Spodoptera frugiperda* Sf21 and *Trichoplusia ni* Tni, yeast cells, animal cells such as mammalian cells, in particular CHO cells, myeloma cells, viro cells, MRCS Cells, HEK cells, African green monkey COS cells, human PerC6 cells and the like.

In some instances it is desirable to employ a mammalian cell because it may produce the protein product with appropriate conformation required for biological activity. Tertiary structure and conformation can be vitally important because incorrect tertiary structure or conformation can result in loss of some or all biological activity. CHO cells have been found to be particularly useful for mammalian expression because the proteins expressed in CHO cells have glycoforms that are generally compatible and bioactive in humans. Accordingly, in one aspect the invention employs a mammalian cell such as a CHO cell, for example a CHOS cell (Invitrogen Cat. No. 11619-012, Deaven, L. L. et al, 1973, Chromasoma 41, 129, D'Anna, J. A. et al, 1996, Methods in Cell Science 18, 115, D'Anna, J. A. et al, 1997, Radiation Research 148, 260) or a derivative therefrom.

The present invention also provides a method of expressing a multimeric protein comprising:
  a) transfecting a cell with the transcriptionally active recombinant linear polynucleotide as defined above; and
  b) expressing the multimeric protein encoded by the transcriptionally active recombinant linear polynucleotide.

In a preferred embodiment, step a) comprises transfecting the cell with a transcriptionally active recombinant linear polynucleotide encoding a heavy chain or fragment thereof of an antibody and a light chain or fragment thereof of an antibody; and step b) comprises expressing the heavy chain polypeptide or fragment thereof and light chain polypeptide or fragment thereof. In this embodiment, the heavy chain polypeptide and the light chain polypeptide preferably assemble to form an antibody or fragment thereof.

The method may also comprise a step of isolating the antibody or fragment thereof from the cell.

The linear transcriptionally active polynucleotide can be incorporated into a cell in various ways using routine means known for transfecting circular DNA.

In addition to the time saving elements and simplification provided by the polynucleotide, the cell and method of the present invention, there may be further advantages provided by the use of the linear transcriptionally active polynucleotide because the amount of genetic material transfected into the cell is relatively small. The linear transcriptionally active polynucleotide may contain about 3,000 to 4,000 base pairs less than a plasmid comprising the same encoding sequences. The cells employed to express the linear transcriptionally active polynucleotide can readily accommodate a plurality of linear transcriptionally active polynucleotides. In fact multiple copies of the linear transcriptionally active polynucleotides are likely to be inserted into each cell. The cell is likely to be able to accommodate more copies of the linear transcriptionally active polynucleotides compared to the number of copies of the corresponding plasmids. Thus the efficiency of expression per cell may be greater when the present method is employed compared to when plasmids comprising the same encoding sequences are employed.

In the method according to the present invention, the cell may be transfected with one or more further linear transcriptionally active polynucleotides encoding distinct proteins. Accordingly, the cell may be transfected with two or more, three or more, four or more, five or more or ten or more distinct linear transcriptionally active polynucleotides.

In one embodiment the linear transcriptionally active polynucleotide is integrated into a chromosome or the genome of the cell to allow stable expression. In a further embodiment of the invention the cell is transiently transfected.

In the embodiment wherein a plurality of distinct linear transcriptionally active polynucleotides are employed the polynucleotides may be introduced into a cell simultaneously or sequentially. In one embodiment the linear transcriptionally active polynucleotides are transfected sequentially. If one polynucleotide encodes a polypeptide known to take longer time to be expressed compared to another polynucleotide, the transfection process may be initiated with only the slower expressing polynucleotide for a period such as 1, 2, 6, 12 or 18 hours followed by addition of the second polynucleotide after this initial period.

The linear transcriptionally active polynucleotide can be introduced into a cell using standard techniques, for example employing electroporation, or lipid based methods (lipotransfection), anionic transfection, cationic transfection such as employing calcium phosphate, heat shock, magnetofection, transfection agents such as lipofectamine, dendrimers, DEAE-dextran transfection, transduction employing a virus. In one embodiment cationic transfection such as employing calcium phosphate is employed. Suitable insect transfection reagents include the Novagen Insect GeneJuice® Transfection Reagent, which is a liposome-based transfection reagent and Cellfectin® (Invitrogen).

When electroporation transfection is employed, the linear transcriptionally active polynucleotide for transfection can be added to a media comprising the relevant cells, before electroporation of the cells to facilitate the transfection process. Suitable conditions for electroporation may, for example, include 200-500 volts such as 250 volts; 1 or 2 pulses of 100 to 200 microseconds, with 0.1 to 5 seconds between pulses, performed in a 1 mm electroporation curvette.

When lipotransfection is employed, the linear transcriptionally active polynucleotide for transfection will generally require pre-formulation to form a liposome before introduction to the cell. Thus if a plurality of distinct polynucleotides are employed each polynucleotide may be separately formulated to form liposomes and optionally combined prior to transfection or a mixture of the linear transcriptionally active polynucleotides may be formulated into liposomes.

When cationic transfection is employed, a mixture of the linear transcriptionally active polynucleotide, the cells and the cationic agent can be introduced concomitantly.

The method according to the present invention may also employ a selection system to facilitate selection of stable cells which have been successfully transfected with the linear transcriptionally active polynucleotide. The selection system typically employs co-transfection of a polynucleotide sequence encoding a selection marker. In one embodiment, the linear transcriptionally active polynucleotide transfected into the cell further comprises a polynucleotide sequence encoding one or more selection markers. Accordingly, the transfection of the linear transcriptionally active polynucleotide and the one or more polynucleotides encoding the marker occurs together and the selection system can be employed to select those cells which produce the desired proteins.

Cells able to express the one or more markers are able to survive/grow/multiply under certain artificially imposed conditions. For example, a suitable toxin or antibiotic may be added to the growth medium accordingly to the properties endowed by the polypeptide/gene or polypeptide component of the selection system incorporated therein (e.g. antibiotic resistance). Those cells that cannot express the one or more markers are not able to survive/grow/multiply in the artificially imposed conditions. The artificially imposed conditions can be chosen to be more or less vigorous, as required.

Any suitable selection system may be employed in the present invention. Suitable selection systems include the use of geneticin, also known as G418, which is a toxin that can be neutralized by the product of a neomycin resistant gene; the use of the enzyme dihydrofolate reductase (DHFR), which is essential for the de novo synthesis of glycine, purine and thymidine, optionally in combination with an inhibitor of DHFR namely, methotrexate; and the use of glutamine synthetase (GS), which catalyses the formation of glutamine from glutamate and ammonia, optionally in combination with an inhibitor of GS, such as methionine sulphoximine (MSX). The zeocin selection system may also be employed in the present invention.

In one embodiment, the method according to the present invention further comprises the step of culturing the transfected cell in a medium to thereby express the multimeric protein encoded by the linear transcriptionally active polynucleotide.

The skilled person would know from their common general knowledge suitable methods in the art to use to select suitable modified cell clones which express the multimeric protein. For example, the skilled person may measure the mRNA expression of the protein from transfected cell clones and determine whether the level of mRNA expression of the protein is higher compared to unmodified cells. Techniques for measuring protein expression include ELISA, PCR analysis and Northern Blot analysis. The cell clones which exhibit expression of the desired protein may then be selected for further growth.

An inducible expression system may be used in the present invention to express the multimeric protein encoded by the linear transcriptionally active polynucleotides. Suitable inducible expression systems are well known in the art.

Any suitable medium may be used to culture the transfected cell, for example Eagle media, fetal calf serum, cellgro or a proprietary media from a company such as Invitrogen. In some instances the media may be serum free. The medium may be adapted for a specific selection system, for example the medium may comprise an antibiotic, to allow only those cells which have been successfully transfected to grow in the medium. The method according to the present invention may also comprise a step of selecting those cells in the medium which have been successfully transfected, such as by selecting cells which are able to grow in the medium.

The cells obtained from the medium may be subjected to further screening and/or purification as required. The method may further comprise one or more steps to extract and purify the protein of interest as required.

One or more method steps described herein may be performed in combination in a suitable container such as a bioreactor.

The present invention also extends to cell cultures that are transfected or transduced with the linear transcriptionally active polynucleotide, as described herein.

In an alternative embodiment, the recombinant protein may be expressed from the one or more transcriptionally active recombinant linear polynucleotides using a cell-free expression system. The cell-free expression system may be derived directly from a cell or may be a defined cell-free expression system not derived from a cell. Cell-free expression systems may be particularly advantageous for the expression of proteins from linear polynucleotides due to reduced adverse effects on the linear polynucleotides caused by cell expression. The cell-free expression system may also not require an agent to uncoil the linear polynucleotides as required for circular polynucleotide vectors. Suitable expression systems are known in the art which may be used to express the recombinant protein from the one or more transcriptionally active recombinant linear polynucleotides, such as the Qiagen® EasyXpress® Insect Kit II which contains *Spodoptera frugiperda* insect cell extract, in vitro transcription reaction components, and reaction buffers (Szatmari, G., Hua, N. M., Vzdornov, D., Daigle, F., Smoragiewicz, W., Mamet-Bratley, M. D., Karska-Wysocki, B. (2006) In vitro expression of the restriction endonucleases LlaMI and ScrFI isolated from *Lactococcus* lactis M19 and UC503. J. Biotechnol. 121, 144 and Lamla, T., Hoerer, S., and Bauer, M. M. (2006) Screening for soluble expression constructs using cell-free protein synthesis. Int. J. Biol. Macromol. 39, 111).

The present invention also provides an expression system comprising the linear transcriptionally active recombinant polynucleotide, as defined above, and a solvent or medium. The expression system may further comprise one or more further distinct linear transcriptionally active recombinant polynucleotides, as defined above. The expression system may be suitable for cell-free expression or cell-dependent expression. In a preferred embodiment, the expression system comprises a host cell as defined above and a solvent or medium.

Any suitable solvent or medium may be used in the expression system including water or tris based buffer for the polynucleotide and a suitable growth media such as CD-CHO FreeStyle™ media for the host cell.

The transcriptionally active recombinant linear polynucleotide employed in the present invention may be made by any suitable method.

The transcriptionally active recombinant linear polynucleotides can be prepared employing PCR, for example using suitable oligonucleotide primers. Nucleic acid amplification methods are well known in the art. Where the nucleic acid which has been recovered is RNA, the RNA may be reverse transcribed to give cDNA. In addition to PCR, other amplification procedures may be used. Other amplification procedures include the T7 and Q-replicase methods.

The present invention also provides a method of producing a transcriptionally active recombinant linear polynucleotide encoding a multimeric protein comprising in the following order, a first promoter sequence, a first encoding polynucleotide sequence, a bidirectional regulatory sequence, a second encoding polynucleotide sequence and a second promoter sequence, wherein the first and second encoding polynucleotide sequences are in convergent transcriptional orientation, each encoding polynucleotide sequence encodes a component of the multimeric protein and the bidirectional regulatory sequence is operably linked to the first and second encoding polynucleotide sequences, wherein the method comprises:

a) providing the first and second promoter sequences, the first encoding polynucleotide sequence comprising the whole or a part of a first multimeric component encoding polynucleotide sequence; the second encoding polynucleotide sequence comprising the whole or a part of a second multimeric component encoding polynucleotide sequence; and a third polynucleotide sequence comprising the bidirectional regulatory sequence and optionally comprising a part of the first and/or second multimeric component encoding polynucleotide sequences;

b) fusing the first encoding polynucleotide sequence to the third polynucleotide sequence;

c) fusing the second encoding polynucleotide sequence to the third polynucleotide sequence; and d) fusing the first promoter sequence to the first encoding polynucleotide sequence and fusing the second promoter sequence to the second encoding polynucleotide sequence.

Steps a), b), c) and step d) according to the above method may be carried out simultaneously or sequentially in any order.

In a preferred embodiment two or more steps of steps b), c) and d) are carried out simultaneously, preferably step b) and step c) are carried out simultaneously, more preferably steps b), c) and d) are carried out simultaneously.

In a preferred embodiment one or more of steps a), b), c) and d) are effected employing PCR. Preferably step b) and/or step c) and/or step d) are effected employing PCR. It is particularly preferred that steps b), c) and d) are effected simultaneously employing PCR.

Referring to FIG. 2, F1 is the first promoter sequence, F2 is the first encoding polynucleotide sequence, F3, is the third polynucleotide sequence comprising the bidirectional regulatory sequence, F4 is the second encoding polynucleotide sequence and F5 is the second promoter sequence.

In one embodiment the first encoding polynucleotide sequence comprises the whole first multimeric component encoding polynucleotide sequence and the second encoding polynucleotide sequence comprises the whole second multimeric component encoding polynucleotide sequence.

In the embodiment of the present invention wherein each of the encoding polynucleotide sequences encodes a fusion protein, each fusion protein comprises a first fusion protein subunit encoding sequence and a second fusion protein subunit encoding sequence. In this embodiment step a) preferably comprises fusing the first fusion protein subunit encoding sequence and the second fusion protein subunit encoding sequence for each multimeric component encoding polynucleotide sequence. This step of fusing the first fusion protein subunit encoding sequence and the second fusion protein subunit encoding sequence is preferably carried out simultaneously with step b) and/or step c) and/or step d).

In one embodiment the first encoding polynucleotide sequence comprises a first fusion protein subunit encoding sequence, the second encoding polynucleotide sequence comprises a first fusion protein subunit encoding sequence and the third polynucleotide sequence comprising the bidirectional regulatory sequence further comprises a second fusion protein subunit encoding sequence at each end of the bidirectional regulatory sequence. Accordingly, in this embodiment F2 as shown in FIG. 2 comprises a first fusion protein subunit encoding sequence, F4 comprises a first fusion protein encoding sequence and F3 comprises the bidirectional regulatory sequence and two second fusion protein subunit encoding sequences, one at each side of the regulatory sequence. In this embodiment, step a) preferably comprises fusing the second fusion protein subunit encoding sequences to the bidirectional regulatory sequence thereby forming the third polynucleotide sequence. This step of fusing the second fusion protein subunit encoding sequences to the bidirectional regulatory sequence maybe carried out simultaneously with step b) and/or step c) and/or step d). This step of fusing the second fusion protein subunit encoding sequences to the bidirectional regulatory sequence is preferably effected employing PCR.

In the embodiment, wherein step a) is effected employing PCR, step a) preferably comprises:

a first PCR amplification of the first encoding polynucleotide sequence in the presence of:
a first primer (P1) comprising a region complementary to the 5' end of the first encoding polynucleotide sequence (F2) and an overlap-extension tail complementary to the 3' end of the first promoter sequence (F1); and a second primer (P2) comprising a region complementary to the 3' end of the first encoding polynucleotide (F2) sequence and an overlap-extension tail complementary to the 5' end (in the forward reading frame) of the third polynucleotide sequence (F3);
thereby producing a first intermediate PCR product comprising the first encoding polynucleotide sequence (F2), the 5' end (in the forward reading frame) of the third polynucleotide sequence (F3) at the 3' end of the first encoding polynucleotide sequence (F2) and the 3' end of the first promoter sequence (F1) at the 5' end of the first encoding polynucleotide sequence (F2); and
a first PCR amplification of the second encoding polynucleotide sequence (F4) in the presence of:
a third primer (P3) comprising a region complementary to the 5' end of the second encoding polynucleotide sequence (F4) and an overlap-extension tail complementary to the 3' end of the second promoter sequence (F5); and a fourth primer (P4) comprising a region complementary to the 3' end of the second encoding polynucleotide sequence (F4) and an overlap-extension tail complementary to the 5' end (in the reverse reading frame) of the third polynucleotide sequence (F3);
thereby producing a second intermediate PCR product comprising the second encoding polynucleotide sequence (F4), the 5' end (in the reverse reading frame) of the third polynucleotide sequence (F3) at the 3' end of the second encoding polynucleotide sequence (F4) and the 3' end of the second promoter sequence (F5) at the 5' end of the second encoding polynucleotide sequence (F4).

In a preferred embodiment step b) and step c) are carried out simultaneously by a second PCR amplification of the first intermediate PCR product and second intermediate PCR product in the presence of the first promoter sequence (F1), the second promoter sequence (F5), the third polynucleotide sequence (F3), a fifth primer (P5) complementary to the 5' end (in the forward reading frame) of the first promoter sequence (F1) and a sixth primer (P6) complementary to 5' end (in the reverse reading frame) of the second promoter sequence (F5) thereby producing a recombinant linear polynucleotide comprising the first promoter sequence (F1), the first encoding polynucleotide sequence (F2), the third polynucleotide sequence (F3), the second encoding polynucleotide sequence (F4) and second promoter sequence (F5), wherein the first promoter sequence (F1) and first encoding polynucleotide sequence (F2) are converging with the second encoding polynucleotide sequence (F4) and the second promoter sequence (F5); and the third polynucleotide sequence (F3) is positioned between the first and second encoding polynucleotide sequences, as shown in FIG. 2.

It is important that the primers are designed appropriately to ensure the success of this PCR amplification method. Typically three pairs of primers are employed in the method. Two pairs of "internal primers" (P1 and P2 for the first encoding sequence F2 and P3 and P4 for the second encoding sequence F4), wherein the first and third primers (P1 and P3) comprises a region complementary to the 5' end of the sequence comprising the first or second encoding polynucleotide sequence (F2 or F4) and an overlap-extension tail complementary to the 3' end of a sequence comprising the first or second promoter (F1 or F5) that will be attached thereto. The second and fourth internal primers (P2 and P4) comprises a region complementary to the 3' end of the sequence comprising the first or second encoding polynucleotide sequence (F2 or F4) and an overlap-extension tail complementary to the 5' end of the forward reading frame or reverse reading frame of the third polynucleotide sequence (F3) that will be attached thereto. The overlap extension tails in the first and third primers (P1 and P3) and second and fourth primers (P2 and P4) ensures the joining of the first or second promoter sequence (F1 or F5), the first or second encoding polynucleotide sequence (F2 or F4) and the third polynucleotide sequence (F3). A pair of "external" primers (discussed below as the fifth primer (P5) and sixth primer (P6), which in relation to the overall linear transcriptionally active polynucleotide sequence assembled are located at the extremities i.e. the absolute 5' end of the sequence in the forward reading frame (P5) and the 5' end of the sequence in the reverse reading frame (P6).

The use of Taq DNA polymerase may add an extra adenosine base (A) at the 3' end of the PCR fragment produced. In this situation, there may be a mismatch between the intermediate PCR products produced by the first PCR step and the first and second promoter sequences (F1 and F5) and the third polynucleotide sequence (F3). Accordingly, in one embodiment of the present invention the first and second promoter sequences (F1 and F5) and the third polynucleotide sequence (F3) are provided with a thymidine base (T) immediately preceding the overlap complementary region with the intermediate PCR product. Accordingly, if adenosine bases are added to the 3' ends of the intermediate PCR product, the intermediate PCR product will still be complementary to the end of the first or second promoter sequence (F1 and F5) and the end of the third polynucleotide sequence (F3).

The first and second PCR steps may be carried out separately or simultaneously.

In one embodiment, after the first PCR step has produced a sufficient quantity of the intermediate PCR product, an agent may be added to the PCR reaction mixture which stops the PCR amplification of PCR 1 with primers P1 and P2 or P3 and P4. An example of such an agent is ExoSap-IT® (USB), which acts to degrade single stranded oligonucleotides including the primers P1 and P2 or P3 and P4 thereby ensuring that PCR1 amplification does not continue in PCR2 amplification with primers P5 and P6. An additional or alternative means to prevent PCR1 amplification with primers P1 and P2 or P3 and P4 to continue during PCR2 amplification with primers P5 and P6 is to limit the quantity of primers P1 and P2 or P3 and P4 used in PCR1 to a suitable quantity required to produce sufficient quantity of the intermediate PCR product during PCR1. A suitable quantity of primers P1 and P2 or P3 and P4 to produce sufficient quantity of the intermediate PCR1 products may be determined by titration methods known in the art.

One or more of the polynucleotide fragments F1, F2, F3, F4 and F5 may comprise one or more non-coding/non-functional nucleotide sequences (i.e. sequences which do not encode polypeptide sequences or function as a transcription element). Accordingly, if one or more of the polynucleotide fragments F1, F2, F3, F4 and F5 comprises non-coding/non-functional nucleotides at the 5' and/or 3 end, one or more of the primers P1, P2, P3, P4, P5 and P6 may comprises sequences which are complementary for the non-coding/non-functional sequence of the fragment or may comprise sequences which are partly complementary for the non-coding/non-functional sequence of the fragment and partly complementary to the transcription element or encoding polynucleotide sequence contained in the fragment. For example, F1 may comprise a non-coding/non-functional nucleotide sequence at the 3' end of F1 and, therefore, the primer P1 may comprise an overlap extension tail complementary to the non-coding/non-functional region at the 3' end of F1. A further example is where the F2 may comprise a non-coding/non-functional nucleotide sequence at the 5' end of the first encoding polynucleotide sequence, such as a leader sequence, and, therefore, the primer P1 may comprise a region complementary to the 5' non-coding/non-functional sequence of F2. A further example is where F1 may comprise a non-coding/non-functional sequence at the 5' end and, therefore P5 primer may be complementary to the non-coding/non-functional sequence at the 5' end of F1. A further example is where F5 may comprise a non-coding/non-functional sequence at the 5' end (in the reverse reading frame) and, therefore P6 primer may be complementary to the non-coding/non-functional sequence at the 5' end of F5.

If the polynucleotide fragments do not comprise one or more non-coding/non-functional nucleotide sequence the primers P1, P2, P3, P4, P5 and P6 may comprise sequences which are fully complementary for the promoter or encoding polynucleotide sequence contained in the respective fragment.

The final linear transcriptionally active polynucleotides produced may be analyzed by any suitable method, such as agarose gel electrophoresis, for confirmation that the PCR product generated is the expected length.

In a preferred embodiment wherein the first multimeric component encoding sequence encodes a light chain or fragment thereof of an antibody and the second multimeric component encoding polynucleotide sequence encodes a heavy chain or a fragment thereof of an antibody, the method described above may also be employed to produce the linear transcriptionally active polynucleotide. The first PCR step for the light chain encoding sequence and the heavy chain encoding sequence may be carried out simultaneously (i.e. in a multiplex step) or separately (i.e. not multiplex). The second PCR step joins the light chain encoding sequence and the heavy chain encoding sequence with the first and second promoter sequences and the third polynucleotide sequence comprising the bidirectional regulatory sequence.

Figure 3A:
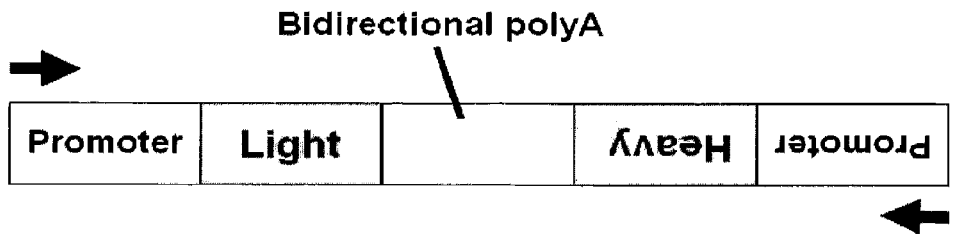
FIG. 3a is schematic diagram of an example transcriptionally active polynucleotide sequence provided by the present invention wherein F2 is a light chain of an antibody or a fragment thereof encoding sequence and F4 is a heavy chain of an antibody or a fragment thereof encoding sequence and FIG. 3b is an example transcriptionally active polynucleotide sequence provided by the present invention comprising rabbit variable light chain encoding sequence (RbVL), mouse constant light chain encoding sequence (mCK), mouse constant heavy chain encoding sequence (mCH1) and rabbit variable heavy chain encoding sequence (RbVH).
Figure 3B:
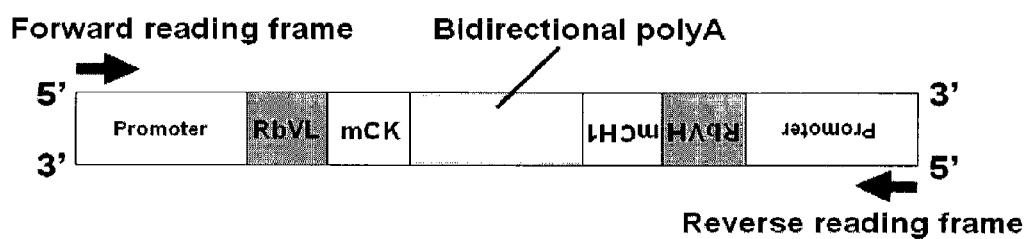

Each linear transcriptionally active polynucleotide preferably comprises a first promoter sequence, a sequence encoding the light chain sequence or fragment thereof, a bidirectional regulatory sequence, a sequence encoding the heavy chain sequence or fragment thereof and a second promoter sequence, as shown in FIG. 3a and FIG. 3b.

The heavy chain or light chain variable domain sequence are referred to as VH or VL and the one or more heavy chain constant domain sequences referred to as CH and light chain constant domain sequence referred to as CL.

The generation of the linear transcriptionally active polynucleotide follows the same PCR steps as described above, wherein:
the first encoding polynucleotide sequence (F2) comprises the whole or a part of the antibody light chain sequence (e.g. VL-CL or VL); and
the second encoding polynucleotide sequence (F4) comprises the whole or a part of antibody heavy chain sequence (e.g. VH-CH or VH); and
the third polynucleotide sequence comprises the bidirectional regulatory sequence and optionally part of the light chain and/or heavy chain encoding sequences (e.g. polyA or CL-polyA-CH)

In one embodiment, wherein:
the first encoding polynucleotide sequence (F2) comprises the variable light chain sequence (VL); and
the second encoding polynucleotide sequence (F4) comprises the variable heavy chain sequence (VH); and
the third polynucleotide sequence (F3) comprises the bidirectional regulatory sequence and constant light chain and constant heavy chain encoding sequences (CL-polyA-CH) the step a) of the method comprises:
a first PCR step for the light chain wherein the antibody variable light sequence (F2) is amplified in the presence of the first primer (P1) and the second primer (P2) to generate the intermediate PCR product comprising the variable light sequence (F2) having a 5' end sequence complementary to the 3' end of the first promoter sequence (F1) and a 3' end sequence complementary to the 5' end (forward reading frame) of the constant light sequence in the third polynucleotide sequence (F3). The design of primers P1 and P2 for the first PCR step relies on knowledge of the antibody variable light domain encoding sequence (F2); and
a first PCR step for the heavy chain wherein the antibody variable light sequence (F4) is amplified in the presence of the third primer (P3) and the forth primer (P4) to generate the intermediate PCR product comprising the variable heavy sequence (F4) having a 5' end sequence complementary to the 3' end of the second promoter sequence (F5) and a 3' end sequence complementary to the 5' end (reverse reading frame) of the constant heavy sequence in the third polynucleotide sequence (F3). The design of primers P3 and P4 for the first PCR step relies on knowledge of the antibody variable heavy domain encoding sequence (F4).

In the second PCR step the variable light intermediate PCR product and variable heavy intermediate PCR product generated in the first PCR steps are amplified in the presence of the first promoter sequence (F1), the third polynucleotide sequence comprising the constant light sequence, the bidirectional regulatory sequence and constant heavy sequence (F3), the second promoter sequence (F5), primer P5 which is an external primer complementary to the 5' end (in the forward reading frame) of the first promoter sequence (F1) and primer P6 which is an external primer complementary to the 5' end (in the reverse reading frame) of the second promoter polynucleotide sequence (F5). The second PCR step generates the complete linear transcriptionally active polynucleotide comprising the first promoter sequence, the light chain variable domain encoding sequence, the light chain constant domain encoding sequence, the bidirectional regulatory sequence, the heavy chain constant domain encoding sequence, heavy chain variable domain encoding sequence and the second promoter sequence.

In this embodiment where the third polynucleotide sequence (F3) comprises the light and heavy constant domain sequences, this sequence may be easily varied to produce a number of different antibodies. Accordingly, different antibodies may be produced quickly and easily using the above described method. The constant domains may be derived from different isotypes and/or species, such as rabbit or mouse. The F3 sequences may also be easily varied to provide different fragments of antibodies. For example, the F3 sequence may comprise the CH1 constant domain to provide a Fab antibody or the F3 may comprise CH1-CH2-CH3 to provide a full length antibody. Therefore, the linear transcriptionally active polynucleotides employed in the present invention allow a diverse range of antibodies to be easily produced and expressed for screening purposes.

In one embodiment the present invention provides one or more primer sequences selected from SEQ ID NO:1, SEQ ID NO:2, SEQ ID NO:3, SEQ ID NO:4, SEQ ID NO:5, SEQ ID NO:6, SEQ ID NO:7 and SEQ ID NO:8. These primer sequences may be used to generate a transcriptionally active recombinant linear polynucleotide by the method described above. The primer sequences are described in detail above and in the examples. The present invention also provides SEQ ID NO: 9 which encodes a constant light chain, a bidirectional polyA and a constant heavy chain.

The promoters, bidirectional regulatory sequence and encoding polynucleotide sequences employed to produce the linear transcriptionally active polynucleotide may be generated by any suitable means.

The promoters and the bidirectional regulatory sequence may be generated by restriction digest of a previously prepared plasmid DNA construct.

The encoding polynucleotide sequences may be generated by any suitable method including PCR amplification.

In one embodiment the method according to the present invention is performed after identification of an antibody of interest (or a fragment thereof), such as by phage display technology.

In the embodiment wherein the encoding polynucleotide sequences comprise variable domains of an antibody, the sequences may be generated by PCR amplification of antibody-encoding nucleic acid sequences generated by SLAM (selected lymphocyte antibody method) as set forth in WO92/02551 (the contents of which are incorporated herein by reference). Accordingly, in one embodiment, the method according to the present invention is employed as further step in the SLAM process which enables a single lymphocyte that is producing an antibody with a desired specificity to be identified within a large population of lymphoid cells and the genetic information that encodes the specificity of the antibody (the variable domains or regions) to be identified from that lymphocyte (Babcook et al., 1996, Proc. Natl. Acad. Sci, 93, 7843-7848).

In the SLAM process a population of antibody-forming cells is cultured in a medium having an indicator system incorporated therein which is capable of indicating the presence and location of a cell which forms antibodies exhibiting the desired function. This allows a cell to be identified from the medium which forms the desired antibodies and the amino acid sequence of the variable domain which confers the desired function of the antibody can be determined. In the SLAM process the variable domain sequence information is then used to synthesize a protein with a desired function usually by incorporating the DNA sequence corresponding to the amino acid sequence of the variable domain into a vector capable of directing the expression and secretion of a protein with the desired function. This final cloning step is a low throughput process in comparison to the previous steps of the SLAM process which are high throughput and capable of automation. However, the cell and method according to the present invention allow a faster and simplified means to produce antibodies or fragments thereof incorporating the variable domain sequence identified by the SLAM process. Accordingly, the present invention allows the final stage of the SLAM process to be high throughput, thus allowing more antibodies to be produced more quickly incorporating various variable domain sequences identified as conferring the desired activity on the antibodies.

Accordingly, the present invention also provides a method for obtaining a recombinant antibody with a desired function, comprising:
a) providing a population of antibody-forming cells suspected of containing at least one cell capable of producing an antibody exhibiting the desired function;
b) generating a transcriptionally active recombinant linear polynucleotide from the antibody forming cells obtained in step (a) wherein the transcriptionally active recombinant linear polynucleotide comprises in the following order:
    (i) a first promoter sequence;
    (ii) a first encoding polynucleotide sequence encoding one or more antibody variable domains or fragments thereof of an antibody produced by an antibody-forming cell obtained in step (a);
    (iii) a bidirectional regulatory sequence
    (iv) a second encoding polynucleotide sequence encoding one or more antibody variable domains or fragments thereof of an antibody produced by an antibody-forming cell obtained in step (a); and
    (v) a second promoter sequence,
wherein the first and second encoding polynucleotide sequences are in convergent transcriptional orientation, each encoding polynucleotide sequence encodes a component of an antibody and the bidirectional regulatory sequence is operably linked to the first and second encoding polynucleotide sequences;
c) expressing a recombinant antibody using the transcriptionally active recombinant linear polynucleotide generated in step (b);
d) screening the recombinant antibody produced by step (c) for the desired function; and
e) optionally repeating steps (b), (c) and (d) to identify a recombinant antibody exhibiting the desired function.

The use of a transcriptionally active recombinant linear polynucleotide to express a recombinant antibody comprising the variable domains of an antibody produced by an antibody forming cell in the method provides many significant improvements to a method for producing a recombinant antibody. The use of a transcriptionally active recombinant linear polynucleotide provides a far quicker means for cloning variable region genes and expressing recombinant antibodies compared to the multiple digestion and ligation steps required to produce vectors and allow a faster and easier way to obtain the recombinant protein.

The population of antibody forming cells provided in step (a) may be from any suitable source. Typically the population of antibody-forming cells is obtained from an animal which has been immunized with a selected antigen or obtained from an animal which generated said cells during the course of a selected disease. The antibody forming cells are typically B-lymphocytes or its progeny including plasma cells. The cells may either secrete antibodies or maintain antibodies on the surface of the cell without secretion into the cellular environment. The antibody-forming cells may be obtained from blood or directly from bone marrow and/or other lymphoid tissue. Further detail regarding the type and origin of antibody-forming cells may be found in WO 92/02551 (the contents of which are incorporated herein by reference).

In step b) the first encoding polynucleotide sequence encodes a variable domain or fragment thereof of an antibody produced by an antibody-forming cell obtained in step a) and the second encoding polynucleotide sequence encodes a variable domain or fragment thereof of an antibody produced by an antibody-forming cell obtained in step a). Preferably the first and second encoding polynucleotide sequences encode variable domains or fragments thereof both derived from one antibody produced by an antibody-forming cell. The transcriptionally active recombinant linear polynucleotide and methods of generating a transcriptionally active recombinant linear polynucleotide have been described in detail above.

The variable domain of an antibody produced by an antibody-forming cell may be incorporated into a transcriptionally active recombinant linear polynucleotide using any suitable method known in the art. In one embodiment the sequence of the variable domain or one or more fragments thereof which confer the specificity of an antibody produced by an antibody-forming cell may be determined. The use of a linear polynucleotide to express the recombinant antibody allows the sequence of the variable domain to be determined during the generation of the one or more transcriptionally active linear polynucleotides in step (b) after any PCR step. However, the sequence of the variable domain or one or more fragments thereof which confer the specificity of the antibody does not need to be determined in order to generate the transcriptionally active recombinant linear polynucleotide. Accordingly, in one embodiment the method does not comprise a step of sequencing the variable domain of the antibody produced by the antibody-forming cell prior to and/or during step (b). Specially designed primers which are complementary to each end of the variable domain or one or more fragments thereof of the antibody, may be used to clone the variable region or one or more fragments thereof by PCR. The primers may be complementary to the framework regions either side of one or more CDRs of the antibody. Further detail regarding how the variable region or a portion thereof of an antibody produced by an antibody-forming cell may be determined may be found in WO 92/02551 (the contents of which are incorporated herein by reference).

In step (b) the first and second encoding polynucleotide sequences may each encode the whole variable domain of an antibody or one or more fragments thereof which confer the specificity of the antibody including one, two or three CDR regions of a variable domain. Each encoding sequence in the transcriptionally active recombinant linear polynucleotide encodes a variable domain or a fragment thereof of an antibody produced by an antibody-forming cell. The variable domain or fragment thereof is the minimum amount of sequence derived from an antibody produced by an antibody-forming cell that each encoding sequence contains. However, each encoding sequence may comprise one or more further antibody domains ether derived from an antibody produced by an antibody-forming cell or from a different source. As described above, each encoding sequence may encode a fusion protein of a variable domain and one or more constant domains.

The transcriptionally active recombinant linear polynucleotide generated in step (b) may comprise a first encoding polynucleotide sequence and a second encoding polynucleotide sequence each encoding a single polypeptide chain antibody or fragment thereof selected from VH, VL, VHH, Fab, scFv. According the transcriptionally active recombinant linear polynucleotide may generate two single domain antibodies such as VHH.

The antibody produced by the antibody-forming cell preferably comprises a heavy chain and a light chain. The transcriptionally active recombinant linear polynucleotide generated in step (b) preferably comprises a first encoding polynucleotide sequence encoding a light chain variable domain or one or more fragments thereof and a second encoding polynucleotide sequence encoding a heavy chain variable domain or one or more fragments thereof from the antibody produced by the antibody-forming cell. As discussed previously the light chain or a fragment thereof is preferably encoded by a variable domain encoding polynucleotide sequence and a constant domain encoding polynucleotide sequence and the heavy chain or a fragment thereof is preferably encoded by a variable domain encoding polynucleotide sequence and one or more constant domain encoding polynucleotide sequences.

In one embodiment the recombinant antibody encoded by the transcriptionally active recombinant linear polynucleotide comprises variable domains or one or more CDRs thereof derived from an antibody produced by an antibody-forming cell and further comprises variable domain framework regions and/or one or more constant domains derived from a different source, such as a known human antibody sequence in order to provide a chimeric or humanized recombinant antibody. The use of a transcriptionally active recombinant linear polynucleotide allows variable domains derived from an antibody produced by an antibody-forming cell to be incorporated into any suitable recombinant antibody format, such as a Fab or a full length antibody with varying constant regions, easily and efficiently.

In this embodiment wherein the antibody comprises a heavy chain and a light chain, the recombinant antibody expressed in step (c) preferably retains the original light chain and heavy chain pairing of an antibody produced by an antibody-forming cell. However, in one embodiment, wherein a plurality of antibody-forming cells are taken forward together in step (b) the recombinant antibodies expressed in step (c) may or may not retain the original light and heavy chain pairing of an antibody produced by an antibody-forming cell.

Step (c) comprises expressing a recombinant antibody using the transcriptionally active recombinant linear polynucleotide generated by step (b). Far higher concentrations of a recombinant antibody can be produced from step (c) of the method of the present invention compared to the quantity of antibody being produced in a population of antibody-forming cells, such as B-lymphocytes obtained from an animal. In one embodiment step (c) comprises transfecting the transcriptionally active recombinant linear polynucleotide into a host cell; and growing said host cells in an appropriate medium as described above. Alternatively or additionally, step (c) comprises expressing the antibody from the transcriptionally active recombinant linear polynucleotide in a cell-free expression system as described above. The use of a cell-free expression system provides a further means for reducing the number of steps required to produce the recombinant protein because steps such as cell transfection are not required for cell-free expression. Accordingly, protein may be produced more quickly and efficiently.

Step (d) comprises screening the recombinant antibody produced by step (c) for the desired function. The screening may be performed by any suitable method known in the art to test the function of an antibody. Functions of the antibody which may be tested include the ability to bind a selected antigen and/or the affinity of the antibody for a selected antigen. Step (d) preferably comprises screening to detect binding of the recombinant antibody to a selected antigen and/or ability to function in a particular assay e.g. neutralization, agonize or antagonize a given biological activity. It will be appreciated that more than one screen may be performed and more than one function tested e.g. binding and functional activity. The selected antigen may be a purified antigen or a cell surface expressed antigen. The selected antigen may or may not be known. Accordingly, the screening step in (d) may include detecting a function of the antibody which does not require knowledge of the antigen such as the effect of the recombinant antibody on the modification of a substrate or the effect on the growth, viability or function of a layer of cells or the effect on the pathogenicity of a pathogenic microorganism. Suitable screening tests are described in detail as indicator systems in WO92/02551.

In one embodiment the method comprises a first screening step prior to step (b) in which the population of antibody-forming cells provided in step (a) are screened to identify an antibody-forming cell or a population of antibody-forming cells producing an antibody exhibiting the desired function. As described above for step (d), the first screening step may include detecting binding to a selected antigen and/or affinity of the antibody to a selected antigen. The identity of the antigen may or may not be known in the first screening step. Accordingly, the first screening step may not require knowledge of the selected antigen. The first screening step may include detecting a function of the antibody which does not require knowledge of the antigen such as the effect of the antibody on the modification of a substrate or the effect on the growth, viability or function of a layer of cells or the effect on the pathogenicity of a pathogenic microorganism. In this embodiment the first screening step identifies a cell or a population of cells and in step (b) the transcriptionally active recombinant linear polynucleotide is generated from the identified cell or population of cells. The first screening step may identify an individual antibody-forming cell or a population of antibody-forming cells which produce an antibody exhibiting the desired function. It will be appreciated that the antibody-forming cell or cells which produce an antibody exhibiting the desired function may be within a population of other cells which do not produce antibodies exhibiting the desired function i.e. it is not necessary for all the cells in a population identified by the first screening step to be producing antibody exhibiting the desired function.

In this embodiment the method preferably further comprises an isolating step prior to step (b) of isolating a single antibody-forming cell producing an antibody exhibiting the desired function identified by the first screening step and in step (b) the transcriptionally active recombinant linear polynucleotide is generated from the single isolated antibody-forming cell. The single antibody-forming cell may be isolated from a population of antibody-forming cells identified by the first screening step. The inclusion of an isolating step is particularly advantageous when the antibody produced by the antibody-forming cell comprises a heavy chain and a light chain because it allows a single recombinant antibody to be expressed which retains the original heavy chain and light chain variable domain pairing of the antibody produced by the antibody-forming cell.

The isolating step may be carried out by any suitable means. In one embodiment the first screening step and the isolating step are carried out simultaneously. In a further embodiment, the first screening step is first carried out to identify an antibody-forming cell or a population of antibody forming cells producing an antibody exhibiting the desired function and the isolating step is subsequently carried out. In this embodiment, the isolating step may comprise a second screening step to identify an antibody-forming cell producing an antibody exhibiting the desired function.

Alternatively, the isolating step comprises isolating a single antibody-forming cell without a second screening step to identify an antibody-forming cell producing an antibody exhibiting the desired function. The single antibody-forming cell may be isolated from a population of antibody-forming cells identified from the first screening step.

An example of a suitable method for carrying out the isolating step, which preferably allows simultaneous screening and isolating, is described in WO 92/02551 (the contents of which are incorporated herein by reference). The method described in WO 92/02551 comprises i) suspending the population of antibody-forming cells obtained in step (a) in a medium, the medium having an indicator system incorporated therein, said indicator system being capable of indicating the presence and location of a cell which forms antibodies exhibiting the desired function;

ii) identifying a single cell forming an antibody exhibiting the desired function; and iii) isolating the identified single antibody-forming cell from the medium.

As described in WO 92/02551 the indicator system manifests a specific desired activity in response to antibody on the surface of or released into the vicinity of an antibody-forming cell, thus permitting identification and isolation of the cell which produces the antibody with the desired function. As described above, the indication of antibodies exhibiting the desired function in step i) may comprise detecting binding to a selected antigen and/or affinity of the antibody to a selected antigen. The identity of the antigen may or may not be known in step i). Step i) may include detecting a function of the antibody which does not require knowledge of the antigen.

As described in WO 92/02551 the indicator system in step i) may comprise:

a layer of cells whose growth, viability, or function is affected by antibodies exhibiting a desired function produced by the isolated antibody-forming cell;

one or more pathogenic microorganisms, and a layer of cells susceptible to infection by said microorganisms, wherein said antibodies exhibiting a desired function are identified as those which effect the pathogenicity of the microorganism;

a set of two cell types selected from the group consisting of cells of distinct HLA histocompatibility antigen types, blood group antigen types, and tumor cells and normal cells of the same lineage, wherein said antibodies exhibiting a desired function are identified as those which agglutinate or lyse one cell of the pair;

erythrocytes or other particles coated with antigen, and said antibody exhibiting the desired function is identified as that which binds to the antigen, thereby causing the particles to agglutinate;

erythrocytes or other particles coated with antigen, and said antibody exhibiting the desired function is identified as that which binds to the antigen, lysing the cells or particles in the presence of complement;

a complexing factor and said antibody-forming cell is identified as that which binds to the complexing factor, forming a rosette; or a substrate, and said antibody exhibiting a desired function is identified as that which modifies the substrate in a detectable manner.

In one embodiment step i) may comprise the method described in WO 2004/051268 (the contents of which are incorporation herein by reference) and WO 2005/121789 (the contents of which are incorporation herein by reference) of incubating said population of antibody producing cells obtained in step (a) with a selected antigen and a labeled anti-antibody antibody, wherein said anti-antibody antibody is capable of distinguishing cells producing an antibody which binds to the selected antigen from those cells which do not; and step ii) comprises identifying a single antibody-forming cell capable of producing an antibody which binds to the selected antigen. As described in WO 2004/051268 and WO 2005/121789, the labeled anti-antibody antibody is preferably an anti-Fc antibody. The anti-antibody antibody is preferably labeled with a fluorescent conjugate.

A further example of a suitable method for carrying out the isolating step, which preferably allows simultaneous screening and isolating, is described in WO 2004/106377 (the contents of which are incorporated herein by reference). The method described in WO 2004/106377 comprises i) bringing the population of antibody-forming cells obtained in step (a) into contact with a capturing agent;
ii) separating the captured antibody-forming cells from the uncaptured antibody-forming cells;
iii) culturing a plurality of captured antibody-forming cells wherein the antibody-forming cells have not been sorted into single antibody-forming cells immediately prior to culturing; and
iv) screening a plurality of the cultured antibody-forming cells to identify a single cell forming an antibody exhibiting the desired function; and
v) isolating the identified single antibody-forming cell.

As described in WO 2004/106377, the separating step is preferably panning and the captured cells are cultured directly following panning. The capturing agent is preferably an antigen.

The step of isolating a single antibody-forming cell may also be carried out by single cell sorting flow cytometry. The single cell sorting flow cytometry may be used to isolate a single antibody-forming cell using any suitable measurable parameters. For example, flow cytometry may be used to isolate a single antibody-forming cell having an antibody-forming cell marker, such as a B-cell marker. Flow cytometry may be used to isolate a single antibody-forming cell capable of binding to a selected antigen. Suitable methods of cell sorting which may be used in the method of the present invention, specifically in the step of isolating, are described in WO05/019824 (the contents of which are incorporation herein by reference) and WO05/019823 (the contents of which are incorporation herein by reference).

A further example of means to isolate a single antibody-forming cell is by automated microscopy and manipulation such as laser capture microscopy.

In one embodiment, prior to step (b) the method comprises an isolating step of directly isolating a single antibody-forming cell from the population of antibody-forming cells obtained in step (a) without first screening the population of antibody-forming cells provided in step (a) for an antibody-forming cell producing an antibody exhibiting the desired function and in step (b) the transcriptionally active recombinant linear polynucleotide is generated from the single isolated antibody-forming cell.

In this embodiment the method does not comprise a separate screening step prior to the isolating step, which is referred to above as the first screening step. However, the step of isolating may itself comprise a simultaneous screening step to identify an antibody-forming cell producing an antibody exhibiting the desired function, which is referred to above as the second screening step. Alternatively, the isolating step comprises isolating a single antibody-forming cell without a separate prior screening step or a simultaneous screening step to identify an antibody-forming cell producing an antibody exhibiting the desired function. Suitable means for isolating a single antibody-forming cell have been described in detail above, including the method described in WO 92/02551, the method described in WO 2004/051268 and WO 2005/121789, the method described in WO 2004/106377, single cell sorting flow cytometry or automated microscopy and manipulation.

In this embodiment the method does not comprise a first screening step prior to generation of the transcriptionally active recombinant linear polynucleotide.

Accordingly, the speed and efficiency of the method is further increased by eliminating early screening step(s). The use of a transcriptionally active recombinant linear polynucleotide allows the early screening step(s) of the antibody-forming cells to be eliminated because it allows high throughput expression of the recombinant antibody. Screening is performed after generation of the recombinant antibody in step (d). A number of advantages result from screening the recombinant antibody for the desired function in step (d) after using one or more transcriptionally active recombinant linear polynucleotides to express the recombinant antibody compared to screening the population of antibody-forming cells for desired function. One advantage is that there is less interference from unknown factors in the recombinant antibody expression media produced in step (c) compared to the media comprising the population of antibody-forming cells. Further, performing screening on the population of antibody producing cells obtained in step (a) may result in antibodies having the desired function being disregarded incorrectly. However, the method of the present invention allows a greater number and variety of recombinant antibodies produced in step (c) to be screened for the desired function as all are expressed at high levels.

The present invention also provides an antibody protein produced according to the method as defined above.

The present invention also encompasses a pharmaceutical composition comprising the linear transcriptionally active recombinant polynucleotide as defined above and/or a cell as defined above. The present invention also encompasses a pharmaceutical composition comprising one or more multimeric proteins produced by the linear transcriptionally active polynucleotide as defined above.

The present invention also encompasses a composition comprising a linear transcriptionally active recombinant polynucleotide as defined above and/or a cell as defined above for use as a medicament. The present invention also encompasses a composition comprising one or more multimeric proteins produced by the linear transcriptionally active polynucleotide as defined above for use as a medicament.

Suitable pharmaceutically acceptable carriers including solvents, solubilizers, fillers, stabilizers and the like are well known in the art. The pharmaceutical composition may be formulated for any intended route of administration including but not limited to parental, intravenous, oral, inhalation, topical and systemic administration. In one embodiment the linear transcriptionally active recombinant polynucleotide as defined above and/or a cell as defined above are suitable for gene delivery for being introduced into a patient. The linear transcriptionally active recombinant polynucleotide may be encapsulated in a liposome for gene delivery. Various other methods of introducing genes into a patient are well known in the art.

The encoding polynucleotide sequence in the linear transcriptionally active polynucleotides may encode a therapeutic or prophylactic multimeric protein suitable for the treatment of a human or non-human animal in need thereof. Accordingly, the protein produced by the cell and method according to the present invention, such as an antibody, may be used for the treatment of disease such as HIV; malaria; allergy; HCV; autoimmune diseases such as irritable bowel syndrome, rheumatoid arthritis and multiple sclerosis; cancer in particular breast cancer, lung cancer, pancreatic cancer, colon cancer, liver cancer, head and neck cancer, leukemia, myeloma and the like.

One or more embodiments of the invention described herein may be combined unless they are technically incompatible.

EXAMPLES

Example 1

Generation of Bidirectional polyA Sequence Comprising Constant Heavy Chain and Constant Light Chain Encoding Sequences A sequence comprising in the following order: a mouse constant light chain encoding sequence (mCK) a bidirectional polyA sequence and a mouse constant heavy chain encoding sequence (mCH1), wherein the mCH1 is orientated in the opposition converging direction to the mCK sequence with respect to the reading frame, as shown in FIG. 3b. This sequence was generated as follows:

The mCK encoding sequence was restriction digested using restriction enzymes HindIII and EcoRI using standard molecular biology techniques from the in house vector pVmCK. This liberated the mCK domain which was flanked by HindIII and EcoRI restriction sites and had an internal BsiWI site at the 5' of the constant domain.

An in house vector pVmFab' was restriction enzyme digested using EcoR1/XhoI restriction enzymes using standard molecular biology techniques to liberate the mCH1' domain which was flanked by EcoRI and XhoI restriction sites.

Figure 4:
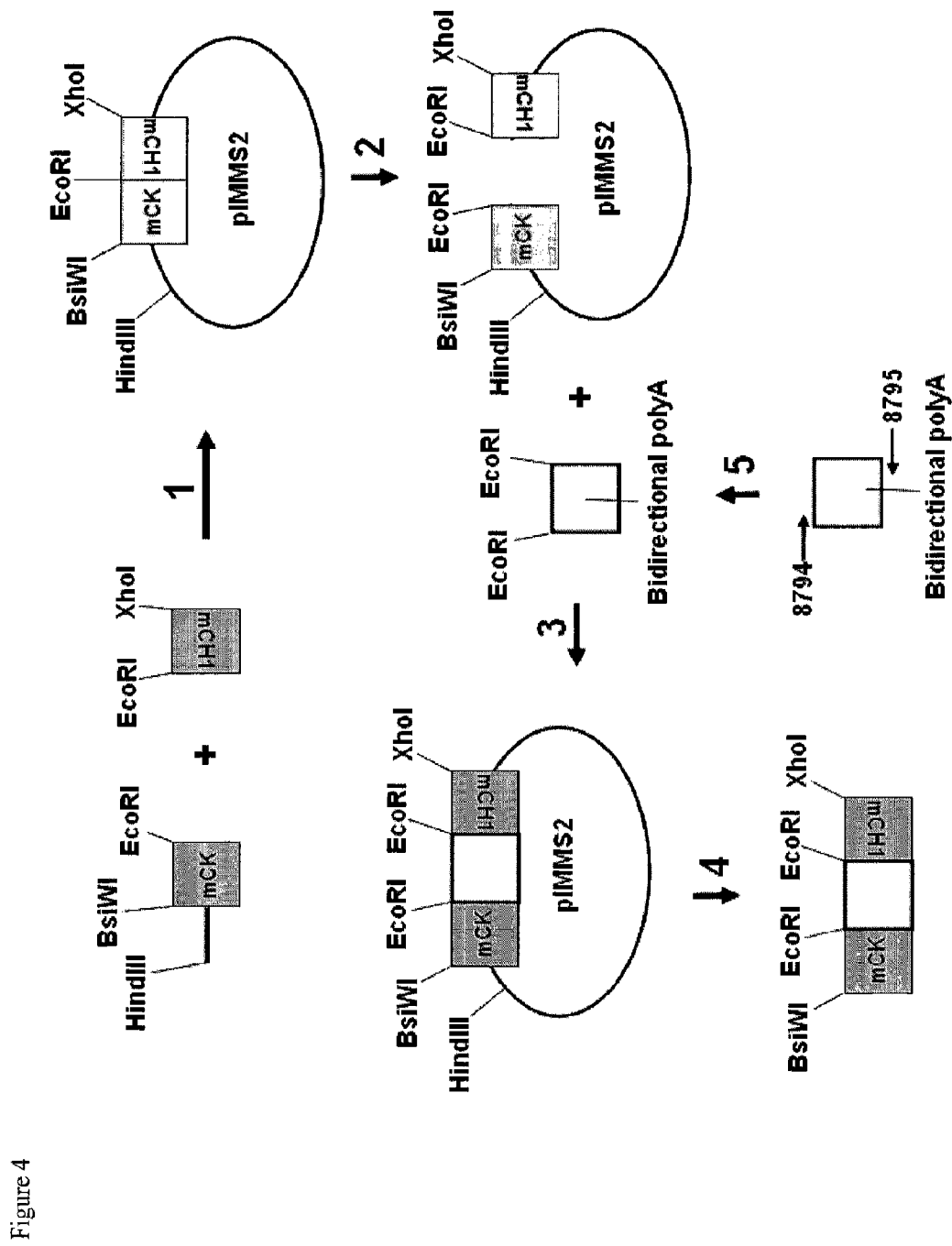
FIG. 4 is a schematic diagram of an example method used to generate a fragment of an example transcriptionally active polynucleotide sequence comprising a bidirectional polyadenylation sequence (polyA) and a mouse constant light (mCK) and mouse constant heavy (mCH1) sequences orientated in opposite converging directions with respect to their reading frames.

The bidirectional polyA sequence was generated in a PCR reaction, as shown in step 5 in FIG. 4. The PCR reaction required the use of two oligonucleotide primers which amplified the polyA sequence and appended two (one each end) EcoRI sites. These primers were numbered 8794 (SEQ ID NO: 1) and 8795 (SEQ ID NO: 2).

SEQ ID NO: 1 is the nucleotide sequence of a forward primer 8794 comprising a region (GAATTCATTGATC) complementary to 5' end of sequence comprising a polyA sequence and an overlap-extension tail comprising an EcoRI site.

SEQ ID NO: 2 is the nucleotide sequence of a reverse primer 8795 comprising a region (GAATTCATCCAGACATGATAAGATAC) complementary to the 3' end of a sequence comprising a polyA sequence and an overlap-extension tail comprising an EcoRI site.

As represented by step 1 of FIG. 4, the in house vector pIMMS2 was digested with HindIII and XhoI and then combined in a three way ligation with both the digested mCK and mCH1 constant domain fragments, which generated a vector comprising the mCK and mCH1 orientated in opposite converging direction with respect to their reading frames.

DNA sequence analysis was performed to confirm the correct construct had been generated. As represented by step 2 of FIG. 4, the vector was then subjected to EcoRI digest. As represented by step 3 of FIG. 4, the digest was followed by a ligation reaction with the EcoRI digested bi-directional polyA fragment generating the pIMMS2 vector comprising the mCK encoding sequence, the polyA sequence and the mCH1 encoding sequence in the correct reading frames, wherein the outer ends of the three sequences comprise BsiWI and XhoI restriction sites. This vector was confirmed by DNA sequence analysis.

As represented by step 5 of FIG. 4, the pIMMS2 vector was used to liberate the three sequences (mCK, polyA and mCH1) using the double restriction digest BsiWI/XhoI. The sequence generated is shown in SEQ ID NO: 9.

Example 2

Generation of the Promoter Sequences

The generation of the two promoter fragments CMV and SFFV was performed by restriction enzyme digest from in house vectors which contained these promoter sequences.

Figure 5A:
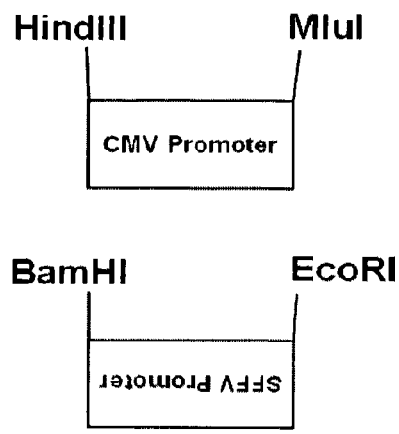
FIG. 5a is a schematic diagram of two promoter sequences, CMV and SFFV which are each flanked by restriction sites.
Figure 5B:
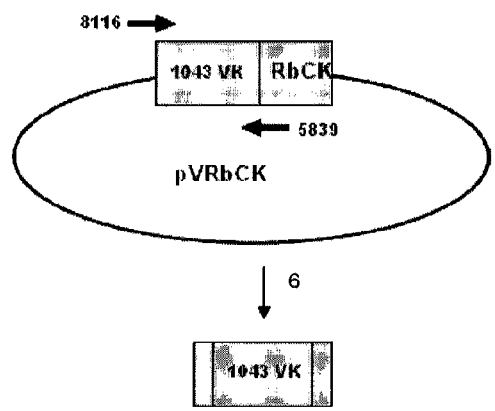
FIG. 5b is a schematic representation of the amplification of the variable light chain (VK) from an in house vector pVRbCK using primers 8116 and 5839.

The forward direction CMV promoter (as shown in FIG. 5a and SEQ ID NO: 10) which drove the transcription of the light chain genes in the final transcriptionally active polynucleotide sequence was digested out of the in house vector pkH11 using HindIII and MluI double digest. The SFFV promoter (as shown in FIG. 5b and SEQ ID NO: 11) was digested out of the in house vector pLentiSam6 using the restriction enzymes EcoRI and BamHI.

Example 3

Generation of Heavy and Light Chain Variable Region Encoding Sequences

The variable region sequences were rabbit antibody variable regions specific for a mouse antigen.

The heavy and light chain variable fragments were amplified using specific oligonucleotide primers which recognised the variable regions and appended additional overlap sequences so that they would combine with the correct promoter and constant region in the final pull through PCR reaction to generate the transcriptionally active polynucleotide sequence.

Light Chain Variable (VK) Region Amplification

Oligonucleotide primers (primers numbered 8116 forward (SEQ ID NO:3) and 5839 reverse (SEQ ID NO:4)) specific for the VK domain of the rabbit antibody were used to amplify the domain from an in house vector (pVRbCK) containing the antibody VK domain, as represented by step 6 in FIG. 5b.

SEQ ID NO: 3 is the nucleotide sequence of a primer 8116 comprising a region (ATGGACAYGAGGGCCCCCACTC) complementary to the 5' end of a variable light chain domain containing sequence, wherein Y is a DNA ambiguity code representing C or T, and an overlap-extension tail complementary to the 3' end of a first promoter (CMV) sequence (CTGCAGTCACCGTCCTTGACACGA).

SEQ ID NO: 4 is the nucleotide sequence of a primer 5839 comprising a region (TTYGACSACCACCTYGGTCCCTC) complementary to the 3' end of a variable light chain domain sequence, wherein Y is a DNA ambiguity code representing C or T and S is a DNA ambiguity code representing G or C, and an overlap-extension tail (CTGGATGGTGGGAAGATGGATACAGTTGGTGCAGCATCCGTAC) complementary to the 5' end of a constant light chain domain sequence.

The PCR Reaction Conditions for Amplification of the Light Chain (VK) Encoding sequence using primers 8116 and 5839 were as follows:

Reaction Mix: Volumes in microliters.

| | |
|---|---|
| Vector (40 ng/ul) | 2.0 |
| 10 × KOD Buffer | 2.5 |
| dNTPs (2 mM each) | 2.5 |
| MgSO4 (25 mM) | 1.0 |
| 8116 Primer (5 uM) | 1.2 |
| 5839 Primer (5 uM) | 1.2 |
| Water | 14 |
| KOD Polymerase | 0.5 |
| Total Volume | 25 |

PCR Conditions:

| | | |
|---|---|---|
| 1. | 96° C. | 2 minutes |
| 2. | 96° C. | 15 s |
| 3. | 55° C. | 15 s |
| 4. | 68° C. | 50 s |
| 5. | go to step 2 | 40 cycles total |
| 6. | 68° C. | 3 minutes |
| 7. | 4° C. | hold |

Heavy Chain Variable (VH) Region Amplification

Figure 5C:
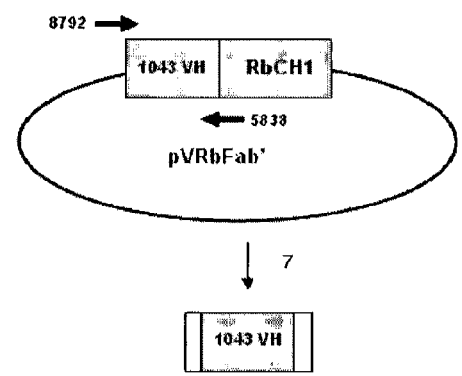
FIG. 5c is a schematic representation of the amplification of the variable heavy chain (VH) from an in house vector pVRbFab' using primers 8792 and 5838.

Oligonucleotide primers (primers numbered 8792 forward (SEQ ID NO: 5) and 5838 reverse (SEQ ID NO:6)) specific for the VH domain of the rabbit antibody were used to amplify the VH domain from an in house vector (pVRbFab') containing the antibody VH domain, as represented by step 7 in FIG. 5c.

SEQ ID NO: 5 is the nucleotide sequence of a primer 8792 comprising a region (ACGCTCACCATGGAGACTGGGC) complementary to the 5' end of a variable heavy chain domain containing sequence and an overlap-extension tail (CCGACAGACTGAGTCGCCCGGGGG) complementary to the 3' end of a second promoter (SFFV) sequence.

SEQ ID NO: 6 is the nucleotide sequence of a primer 5838 comprising a region (ACGGTGACSAGGGTSCCYKGGCCC) complementary to the 3' end of a variable heavy chain domain sequence, wherein S is a DNA ambiguity code representing G or C, Y is a DNA ambiguity code representing C or T and K is a DNA ambiguity code representing G or T, and an overlap-extension tail (GACAGATGGGGGTGTCGTTTTGGCACTCGA) complementary to the 5' end of a constant heavy chain domain sequence.

The PCR reaction conditions for amplification of the heavy chain (VH) encoding sequence using primers 8792 and 5838 were the same as shown above for the amplification of the light chain (VK) encoding sequence.

Example 4

Final PCR Generation of Transcriptionally Active Polynucleotide (TAP)

Figure 6:
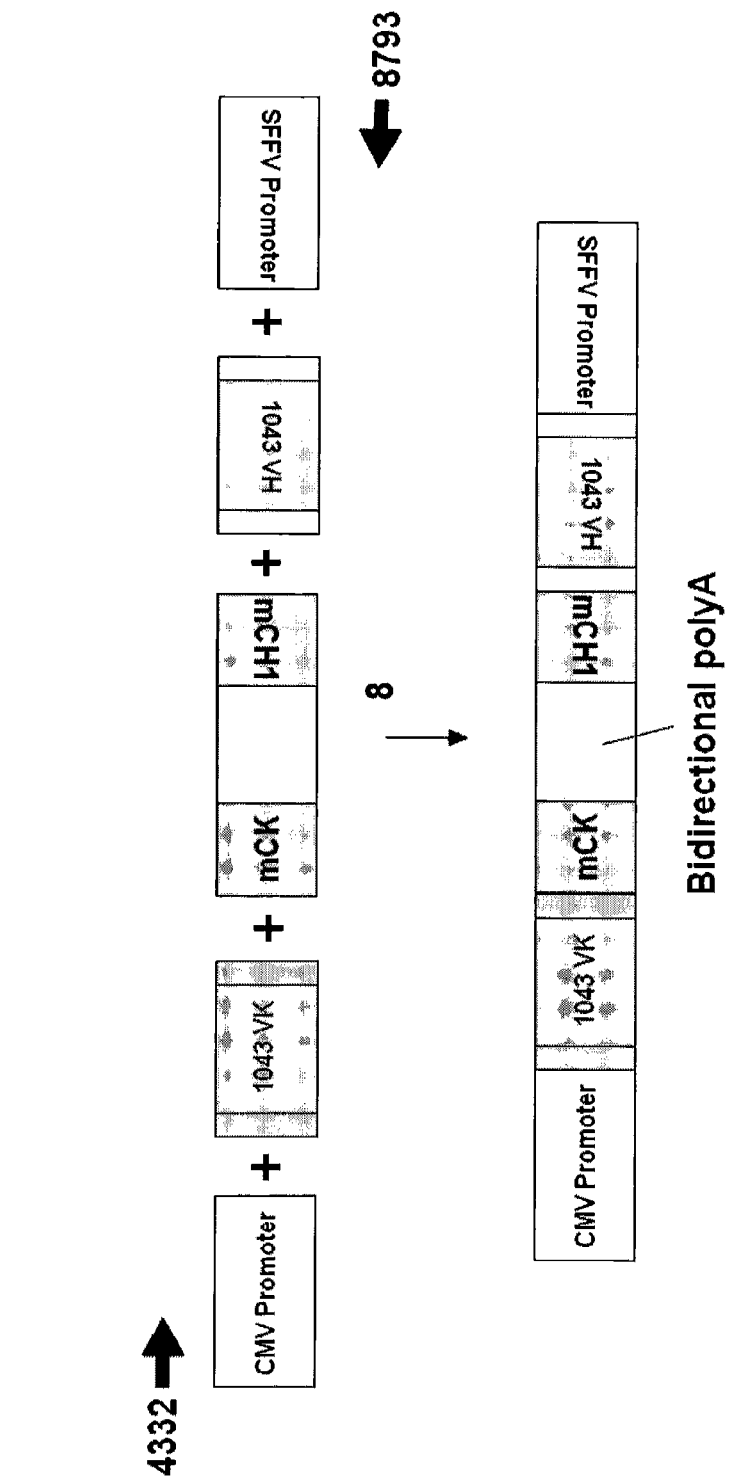
FIG. 6 is a schematic diagram of the generation of the final transcriptionally active linear recombinant polynucleotide sequence comprising in the following order a CMV promoter, a variable light encoding sequence (VK), a constant light encoding sequence (mCK), a bidirectional polyA sequence, a constant heavy encoding sequence (mCH1), a variable heavy encoding sequence (VH) and a SFFV promoter sequence by pull through PCR using primers 4332 and 8793.

In the final PCR the two promoters, the central sequence comprising the mCK constant light, the polyA and the mCH1 constant heavy and the two amplified VK and VH PCR products were in effect stitched together by pull through PCR, as shown in FIG. 6. This PCR was driven by two external oligonucleotides 4332 (SEQ ID NO: 7) and 8793 (SEQ ID NO: 8).

SEQ ID NO: 7 is the nucleotide sequence of a primer 4332 which is complementary to a sequence upstream of the first (CMV) promoter sequence.

SEQ ID NO: 8 is the nucleotide sequence of a primer 8793 which is complementary to a sequence upstream of the second (SFFV) promoter sequence and the 5' end of the SFFV promoter sequence.

The PCR conditions were as follows:
PCR reaction mix: Volumes in microliters

| | |
|---|---|
| VH PCR product | 1.0 |
| VK PCR product | 1.0 |
| 10 × Buffer | 2.5 |
| dNTPs (2 mM each) | 2.5 |
| MgSO4 (25 mM) | 1.0 |
| Primer 4332 (2.5 uM) | 2.5 |
| Primer 8793 (2.5 uM) | 2.5 |

-continued

| | |
|---|---|
| CMV promoter fragment | 10 ng |
| SFFV promoter fragment | 10 ng |
| mCK, poly A, mCH1 fragment | 10 ng |
| Water | Make up to 24.5 |
| Then add KOD | 0.5 |
| Total | 25 |

Conditions:

| | | |
|---|---|---|
| 1. | 96° C. | 2 minutes |
| 2. | 96° C. | 1 minute |
| 3. | 50° C. | 1 minute |
| 4. | 68° C. | 4 minute |
| 5. | go to step 2 | 25 cycles total |
| 6. | 68° C. | 10 minutes |
| 7. | 4° C. | hold |

The design of the oligonucleotide primers used in example 4 to amplify the variable regions ensures that all of the different (5) sequences of the PCR align correctly and come together to produce the full length TAP sequence.

The final TAP sequence produced was analysed by agarose gel electrophoresis to confirm that a construct of the right size had been produced.

Example 5

Transfection of TAP Fragment and FAB Expression

The transcriptionally active polynucleotide sequence produced by Example 5 was then transiently transfected into HEK 293 cells using the "293fectin" kit as follows:
Diluted 10 uL DNA per well into 70 μl Opti-MEM medium, in eppendorfs (POLYCARBONATE tubes). Into 70 ul Opti-MEM, diluted 4 ul 293fectin per well (NB it was important to place medium in first) again using eppendorfs (POLYCARBONATE tube). Incubated for 5 mins at RT (no more). Combined DNA+293fectin and mixed gently (do not allow 293fectin to stand in medium for more than 5 mins). Incubated for 20 mins at RT.

Resuspended HEK293 cells in warm FreeStyle™ media, at 1×10⁶/ml, prepared 2 ml of cells per transfection well. Added cells to the 24 well block. Added the complex to the cells. Incubated at 37° C. on a shaking platform to maintain cell suspension (225 rpm). Harvested supernatant after 4 days incubation.

After 4 to 5 days the supernatant of these cells was tested in two ELISA based assays, one to show that antibody (Fab) had been produced and another to show that it was able to bind to the original target, as follows:

96 well Nunc Maxisorb ELISA plate coated overnight in 2 ug/ml Goat anti Mouse Fab (Jackson) in PBS at 5° C., 100 ul/well. Plate washed four times in PBS 0.1% Tween 20. Plate blocked in 2% BSA (PBS) (SIGMA) at room temp for 1 hour, 300 ul/well. Plate washed four times in PBS 0.1% Tween 20. Chimeric TN3 1ug/mL used as standard, samples and standard added in half log dilutions into block down the plate, bottom row only block added, 100 uL/well. Plate left at room temp for 1 hour. Plate washed four times in PBS 0.1% Tween 20. Goat anti Mouse Kappa HRP (Jackson) 1 in 5,000 dilution in block, added 100 ul/well, plate left at room temp for 1 hour. Plate washed four times in PBS 0.1% Tween 20. Plate developed with TMB (Calbiochem) 100 ul/well, absorbance read at 630 nm.

96 well Nunc Maxisorb ELISA plate coated overnight in 2 ug/ml Goat anti Human Fc (Jackson) in PBS at 5° C. Plate washed four times in PBS 0.1% Tween 20. Plate blocked in 2% BSA (PBS) (SIGMA) at room temp for 1 hour, 300 ul/well. Plate washed four times in PBS 0.1% Tween 20. Mouse antigen human Fc chimeric (Jackson) added at 250 ng/ml in block 100 ul/well, plate left at room temp for 1 hour. Plate washed four times in PBS 0.1% Tween 20. Rabbit anti mouse antigen 685 lug/mL used as standard, samples and standard added in half log dilutions into block down the plate, bottom row only block added, 100 uL/well. Plate left at room temp for 1 hour. Plate washed four times in PBS 0.1% Tween 20. Goat anti Mouse Kappa HRP (Jackson) 1 in 5,000 dilution in block, added 100 ul/well, plate left at room temp for 1 hour, except for standard, Goat anti Rabbit Fab HRP (Jackson). Plate washed four times in PBS 0.1% Tween 20. Plate developed with TMB (Calbiochem) 100 ul/well, absorbance read at 630 nm.

The results from the experiments described above indicated that Fab had been produced by the HEK293 cells and that it was specific for the target antigen.

SEQUENCES

SEQ ID NO: 1
CCATGATAAGAATTCATTGATC

SEQ ID NO: 2
CACTGATGAATTCATCCAGACATGATAAGATAC

SEQ ID NO: 3
CTGCAGTCACCGTCCTTGACACGAAGCTTCGAAGCCACCATGGACAYGA
GGGCCCCCACTC

SEQ ID NO: 4
CTGGATGGTGGGAAGATGGATACAGTTGGTGCAGCATCCGTACGTTYGA
CSACCACCTYGGTCCCTC

SEQ ID NO: 5
CCGACAGACTGAGTCGCCCGGGGGAAGCTTACGCTCACCATGGAGACTG
GGC

SEQ ID NO: 6
GACAGATGGGGGTGTCGTTTTGGCACTCGAGACGGTGACSAGGGTSCCY
KGGCCCC

SEQ ID NO: 7
ACGCGTTTTGAGATTTCTGTCGCCGACTAAATTCATGTCGCG

SEQ ID NO: 8
TTCCTGCAGCCCCGATAAAATAAAAG

SEQ ID NO: 9
TCGAGTGCCAAAACGACACCCCCATCTGTCTATCCACTGGCCCCTGGAT
CTGCTGCCCAAACTAACTCCATGGTGACCCTGGGATGCCTGGTCAAGGG
CTATTTCCCTGAGCCAGTGACAGTGACCTGGAACTCTGGATCCCTGTCC
AGCGGTGTGCACACCTTCCCAGCTGTCCTGCAGTCTGACCTCTACACTC
TGAGCAGCTCAGTGACTGTCCCCTCCAGCACCTGGCCCAGCGAGACCGT
CACCTGCAACGTTGCCCACCCGGCCAGCAGCACCAAGGTGGACAAGAAA
ATTGTGCCCAGGGATTGTGGTTGTGCAGCCTAATGAATTCATCCAGACA
TGATAAGATACATTGATGAGTTTGGACAAACCACAACTAGAATGCAGTG
AAAAAAATGCTTTATTTGTGAAATTTGTGATGCTATTGCTTTATTTGTA
ACCATTATAAGCTGCAATAAACAAGTTAACAACAACAATTGCATTCATT
TTATGTTTCAGGTTCAGGGGGAGGTGTGGGAGGTTTTTTAAAGCAAGTA
AAACCTCTACAAATGTGGTATGGCTGATTATGATCAATGAATTCCCAGG
CTGGAACTCTGAGGAGCAGCTAACACTCATTCCTGTTGAAGCTCTTGACAA
TGGGTGAAGTTGATGTCTTGTGAGTGGCCTCACAGGTATAGCTGTTATG

TCGTTCATACTCGTCCTTGGTCAACGTGAGGGTGCTGCTCATGCTGTAG
GTGCTGTCTTTGCTGTCCTGATCAGTCCAACTGTTCAGGACGCCATTTT
GTCGTTCACTGCCATCAATCTTCCACTTGACATTGATGTCTTTGGGGTA
GAAGTTGTTCAAGAAGCACACGACTGAGGCACCTCCAGATGTTAACTGC
TCACTGGATGGTGGGAAGATGGATACAGTTGGTGCAGCATCC

SEQ ID NO: 10
CGCGTTTTGAGATTTCTGTCGCCGACTAAATTCATGTCGCGCGATAGTG
GTGTTTATCGCCGATAGAGATGGCGATATTGGAAAAATCGCGGCGGCCG
CCGATATTTGAAAATATGGCATATTGAAAATGTCGCCGATGTGAGTTTC
TGTGTAACTGATATCGCCATTTTTCCAAAAGTGATTTTTGGGCATACGC
GATATCTGGCGATAGCGCTTATATCGTTTACGGGGGATGGCGATAGACG
ACTTTGGTGACTTGGGCGATTCTGTGTGTCGCAAATATCGCAGTTTCGA
TATAGGTGACAGACGATATGAGGCTATATCGCCGATAGAGGCGACATCA
AGCTGGCACATGGCCAATGCATATCGATCTATACATTGAATCAATATTG
GCCATTAGCCATATTATTCATTGGTTATATAGCATAAATCAATATTGGC
TATTGGCCATTGCATACGTTGTATCCATATCATAATATGTACATTTATA
TTGGCTCATGTCCAACATTACCGCCATGTTGACATTGATTATTGACTAG
TTATTAATAGTAATCAATTACGGGGTCATTAGTTCATAGCCCATATATG
GAGTTCCGCGTTACATAACTTACGGTAAATGGCCCGCCTGGCTGACCGC
CCAACGACCCCCGCCCATTGACGTCAATAATGACGTATGTTCCCATAGT
AACGCCAATAGGGACTTTCCATTGACGTCAATGGGTGGAGTATTTACGG
TAAACTGCCCACTTGGCAGTACATCAAGTGTATCATATGCCAAGTACGC
CCCCTATTGACGTCAATGACGGTAAATGGCCCGCCTGGCATTATGCCCA
GTACATGACCTTATGGGACTTTCCTACTTGGCAGTACATCTACGTATTA
GTCATCGCTATTACCATGGTGATGCGGTTTTGGCAGTACATCAATGGGC
GTGGATAGCGGTTTGACTCACGGGGATTTCCAAGTCTCCACCCCATTGA
CGTCAATGGGAGTTTGTTTTGGCACCAAAATCAACGGGACTTTCCAAAA
TGTCGTAACAACTCCGCCCCATTGACGCAAATGGGCGGTAGGCGTGTAC
GGTGGGAGGTCTATATAAGCAGAGCTCGTTTAGTGAACCGTCAGATCGC
CTGGAGACGCCATCCACGCTGTTTTGACCTCCATAGAAGACACCGGGAC
CGATCCAGCCTCCGCGGCCGGGAACGGTGCATTGGAACGCGGATTCCCC
GTGCCAAGAGTGACGTAAGTACCGCCTATAGAGTCTATAGGCCCACCCC
CTTGGCTTCTTATGCATGCTATACTGTTTTTGGCTTGGGGTCTATACAC
CCCCGCTTCCTCATGTTATAGGTGATGGTATAGCTTAGCCTATAGGTGT
GGGTTATTGACCATTATTGACCACTCCCCTATTGGTGACGATACTTTCC
ATTACTAATCCATAACATGGCTCTTTGCCACAACTCTCTTTATTGGCTA
TATGCCAATACACTGTCCTTCAGAGACTGACACGGACTCTGTATTTTTA
CAGGATGGGGTCTCATTTATTATTTACAAATTCACATATACAACACCAC
CGTCCCCAGTGCCCGCAGTTTTTATTAAACATAACGTGGGATCTCCACG
CGAATCTCGGGTACGTGTTCCGGACATGGGCTCTTCTCCGGTAGCGCCG
GAGCTTCTACATCCGAGCCCTGCTCCCATGCCTCCAGCGACTCATGGTC
GCTCGGCAGCTCCTTGCTCCTAACAGTGGAGGCCAGACTTAGGCACAGC
ACGATGCCCACCACCACCAGTGTGCCGCACAAGGCCGTGGCGGTAGGGT
ATGTGTCTGAAAATGAGCTCGGGGAGCGGGCTTGCACCGCTGACGCATT
TGGAAGACTTAAGGCAGCGGCAGAAGAAGATGCAGGCAGCTGAGTTGTT
GTGTTCTGATAAGAGTCAGAGGTAACTCCCGTTGCGGTGCTGTTAACGG
TGGAGGGCAGTGTAGTCTGAGCAGTACTCGTTGCTGCCGCGCGCGCCAC
CAGACATAATAGCTGACAGACTAACAGACTGTTCCTTTCCATGGGTCTT
TTCTGCAGTCACCGTCCTTGACACGA

SEQ ID NO: 11
AATTCCTGCAGCCCCGATAAAATAAAAGATTTTATTTAGTCTCCAGAAA
AAGGGGGGAATGAAAGACCCCACCTGTAGGTTTGGCAAGCTAGCTGCAG
TAACGCCATTTTGCAAGGCATGGAAAAATACCAAACCAAGAATAGAAAA
GTTCAGATCAAGGGCGGGTACATGAAAATAGCTAACGTTGGGCCAAACA
GGATATCTGCGGTGAGCAGTTTCGGCCCCGGCCCGGGGCCAAGAACAGA
TGGTCACCGCAGTTTCGGCCCCGGCCCGAGGCCAAGAACAGATGGTCCC
CAGATATGGCCCAACCCTCAGCAGTTTCTTAAGACCCATCAGATGTTTC
CAGGCTCCCCCAAGGACCTGAAATGACCCTGCGCCTTATTTGAATTAAC
CAATCAGCCTGCTTCTCGCTTCTGTTCGCGCGCTTCTGCTTCCCGAGCT
CTATAAAAGAGCTCACAACCCCTCACTCGGCGCGCCAGTCCTCCGACAG
ACTGAGTCGCCCGGGGG

```
<220> FEATURE:
<223> OTHER INFORMATION: Forward Primer complementary to 5' end of polyA

<400> SEQUENCE: 1
ccatgataag aattcattga tc                                              22

<210> SEQ ID NO 2
<211> LENGTH: 33
<212> TYPE: DNA
<213> ORGANISM: Artificial Sequence
<220> FEATURE:
<223> OTHER INFORMATION: Reverse Primer completmentary to PolyA

<400> SEQUENCE: 2
cactgatgaa ttcatccaga catgataaga tac                                  33

<210> SEQ ID NO 3
<211> LENGTH: 61
<212> TYPE: DNA
<213> ORGANISM: Artificial Sequence
<220> FEATURE:
<223> OTHER INFORMATION: Primer complementary to 5' end of VL sequence
      and 3' end of CMV

<400> SEQUENCE: 3
ctgcagtcac cgtccttgac acgaagcttc gaagccacca tggacaygag ggcccccact     60
c                                                                     61

<210> SEQ ID NO 4
<211> LENGTH: 67
<212> TYPE: DNA
<213> ORGANISM: Artificial Sequence
<220> FEATURE:
<223> OTHER INFORMATION: Primer to 3' end of VL and 5' end of CL

<400> SEQUENCE: 4
ctggatggtg ggaagatgga tacagttggt gcagcatccg tacgttygac saccacctyg     60
gtccctc                                                               67

<210> SEQ ID NO 5
<211> LENGTH: 52
<212> TYPE: DNA
<213> ORGANISM: Artificial Sequence
<220> FEATURE:
<223> OTHER INFORMATION: Primer complementary to 5' end of VH and 3' end
      of SFFV promoter

<400> SEQUENCE: 5
ccgacagact gagtcgcccg ggggaagctt acgctcacca tggagactgg gc             52

<210> SEQ ID NO 6
<211> LENGTH: 56
<212> TYPE: DNA
<213> ORGANISM: Artificial Sequence
<220> FEATURE:
<223> OTHER INFORMATION: Primer complementary to 3' end VH and 5' end of
      CH

<400> SEQUENCE: 6
gacagatggg ggtgtcgttt tggcactcga gacggtgacs agggtsccyk ggcccc         56

<210> SEQ ID NO 7
<211> LENGTH: 42
<212> TYPE: DNA
<213> ORGANISM: Artificial Sequence
```

<220> FEATURE:
<223> OTHER INFORMATION: Primer complementary to non-coding region of
    CMV promoter sequence

<400> SEQUENCE: 7
acgcgttttg agatttctgt cgccgactaa attcatgtcg cg                          42

<210> SEQ ID NO 8
<211> LENGTH: 26
<212> TYPE: DNA
<213> ORGANISM: Artificial Sequence
<220> FEATURE:
<223> OTHER INFORMATION: Primer complementary to 5' end of SFFV promoter
    sequence

<400> SEQUENCE: 8
ttcctgcagc cccgataaaa taaaag                                            26

<210> SEQ ID NO 9
<211> LENGTH: 924
<212> TYPE: DNA
<213> ORGANISM: Artificial Sequence
<220> FEATURE:
<223> OTHER INFORMATION: Seqence encoding: constant light chain,
    bidirectional polyA and constant heavy chain

<400> SEQUENCE: 9
tcgagtgcca aaacgacacc cccatctgtc tatccactgg cccctggatc tgctgcccaa        60
actaactcca tggtgaccct gggatgcctg gtcaagggct atttccctga gccagtgaca       120
gtgacctgga actctggatc cctgtccagc ggtgtgcaca ccttcccagc tgtcctgcag       180
tctgacctct acactctgag cagctcagtg actgtcccct ccagcacctg gcccagcgag       240
accgtcacct gcaacgttgc cacccggcc agcagcacca aggtggacaa gaaaattgtg        300
cccagggatt gtggttgtgc agcctaatga attcatccag acatgataag atacattgat       360
gagtttggac aaaccacaac tagaatgcag tgaaaaaaat gctttatttg tgaaatttgt       420
gatgctattg ctttatttgt aaccattata agctgcaata acaagttaa caacaacaat       480 tgcattcatt ttatgtttca ggttcagggg gaggtgtggg aggttttta aagcaagtaa       540 aacctctaca aatgtggtat ggctgattat gatcaatgaa ttcccaggct ggaactgagg       600
agcagctaac actcattcct gttgaagctc ttgacaatgg gtgaagttga tgtcttgtga       660
gtggcctcac aggtatagct gttatgtcgt tcatactcgt ccttggtcaa cgtgagggtg       720
ctgctcatgc tgtaggtgct gtctttgctg tcctgatcag tccaactgtt caggacgcca       780
ttttgtcgtt cactgccatc aatcttccac ttgacattga tgtctttggg gtagaagttg       840
ttcaagaagc acacgactga ggcacctcca gatgttaact gctcactgga tggtgggaag       900
atggatacag ttggtgcagc atcc                                             924

<210> SEQ ID NO 10
<211> LENGTH: 2084
<212> TYPE: DNA
<213> ORGANISM: Artificial Sequence
<220> FEATURE:
<223> OTHER INFORMATION: CMV promoter

<400> SEQUENCE: 10
cgcgttttga gatttctgtc gccgactaaa ttcatgtcgc gcgatagtgg tgtttatcgc        60
cgatagagat ggcgatattg gaaaaatcgc ggcggccgcc gatatttgaa aatatggcat       120
attgaaaatg tcgccgatgt gagtttctgt gtaactgata tcgccatttt tccaaaagtg       180

```
atttttgggc atacgcgata tctggcgata gcgcttatat cgtttacggg ggatggcgat    240
agacgacttt ggtgacttgg gcgattctgt gtgtcgcaaa tatcgcagtt tcgatatagg    300
tgacagacga tatgaggcta tatcgccgat agaggcgaca tcaagctggc acatggccaa    360
tgcatatcga tctatacatt gaatcaatat tggccattag ccatattatt cattggttat    420
atagcataaa tcaatattgg ctattggcca ttgcatacgt tgtatccata tcataatatg    480
tacatttata ttggctcatg tccaacatta ccgccatgtt gacattgatt attgactagt    540
tattaatagt aatcaattac ggggtcatta gttcatagcc catatatgga gttccgcgtt    600
acataactta cggtaaatgg cccgcctggc tgaccgccca acgaccccg  cccattgacg    660 tcaataatga cgtatgttcc catagtaacg ccaataggga ctttccattg acgtcaatgg    720
gtggagtatt tacggtaaac tgcccacttg gcagtacatc aagtgtatca tatgccaagt    780
acgcccccta ttgacgtcaa tgacggtaaa tggcccgcct ggcattatgc ccagtacatg    840
accttatggg actttcctac ttggcagtac atctacgtat tagtcatcgc tattaccatg    900
gtgatgcggt tttggcagta catcaatggg cgtggatagc ggtttgactc acggggattt    960
ccaagtctcc accccattga cgtcaatggg agtttgtttt ggcaccaaaa tcaacgggac   1020
tttccaaaat gtcgtaacaa ctccgcccca ttgacgcaaa tgggcggtag gcgtgtacgg   1080
tgggaggtct atataagcag agctcgttta gtgaaccgtc agatcgcctg gagacgccat   1140
ccacgctgtt ttgacctcca tagaagacac cgggaccgat ccagcctccg cggccgggaa   1200
cggtgcattg gaacgcggat tccccgtgcc aagagtgacg taagtaccgc ctatagagtc   1260
tataggccca cccccttggc ttcttatgca tgctatactg tttttggctt ggggtctata   1320
cacccccgct tcctcatgtt ataggtgatg gtatagctta gcctataggt gtgggttatt   1380
gaccattatt gaccactccc ctattggtga cgatactttc cattactaat ccataacatg   1440
gctctttgcc acaactctct ttattggcta tatgccaata cactgtcctt cagagactga   1500
cacggactct gtatttttac aggatggggt ctcattatt  atttacaaat tcacatatac   1560
aacaccaccg tccccagtgc ccgcagtttt tattaaacat aacgtgggat ctccacgcga   1620
atctcgggta cgtgttccgg acatgggctc ttctccggta gcggcggagc ttctacatcc   1680
gagccctgct cccatgcctc cagcgactca tggtcgctcg gcagctcctt gctcctaaca   1740
gtggaggcca gacttaggca cagcacgatg cccaccacca ccagtgtgcc gcacaaggcc   1800
gtggcggtag ggtatgtgtc tgaaaatgag ctcggggagc gggcttgcac cgctgacgca   1860
tttggaagac ttaaggcagc ggcagaagaa gatgcaggca gctgagttgt tgtgttctga   1920
taagagtcag aggtaactcc cgttgcggtg ctgttaacgg tggagggcag tgtagtctga   1980
gcagtactcg ttgctgccgc gcgcgccacc agacataata gctgacagac taacagactg   2040
ttcctttcca tgggtctttt ctgcagtcac cgtccttgac acga                    2084
```

<210> SEQ ID NO 11
<211> LENGTH: 507
<212> TYPE: DNA
<213> ORGANISM: Artificial Sequence
<220> FEATURE:
<223> OTHER INFORMATION: SFFV promoter

<400> SEQUENCE: 11

```
aattcctgca gccccgataa aataaaagat ttatttagt ctccagaaaa agggggggaat     60 gaaagacccc acctgtaggt ttggcaagct agctgcagta acgccatttt gcaaggcatg    120 gaaaatacc  aaaccaagaa tagagaagtt cagatcaagg gcgggtacat gaaaatagct    180
```

-continued

| | | | | | |
|---|---|---|---|---|---|
| aacgttgggc | caaacaggat | atctgcggtg | agcagtttcg | gccccggccc | ggggccaaga | 240 |
| acagatggtc | accgcagttt | cggccccggc | ccgaggccaa | gaacagatgg | tccccagata | 300 |
| tggcccaacc | ctcagcagtt | tcttaagacc | catcagatgt | ttccaggctc | ccccaaggac | 360 |
| ctgaaatgac | cctgcgcctt | atttgaatta | accaatcagc | ctgcttctcg | cttctgttcg | 420 |
| cgcgcttctg | cttcccgagc | tctataaaag | agctcacaac | ccctcactcg | gcgcgccagt | 480 |
| cctccgacag | actgagtcgc | ccggggg | | | | 507 |

The invention claimed is:

1. A transcriptionally active recombinant linear polynucleotide encoding a multimeric protein comprising in the following order,
a first promoter sequence,
a first encoding polynucleotide sequence,
a bidirectional polyadenylation sequence that is capable of forming the end of each RNA transcript formed,
a second encoding polynucleotide sequence and a second promoter sequence,
wherein the first and second encoding polynucleotide sequences are in convergent transcriptional orientation, each encoding polynucleotide sequence encodes a component of the multimeric protein
and the bidirectional polyadenylation sequence is operably linked to the first and second encoding polynucleotide sequences
and the multimeric protein is an antibody or fragment thereof and each encoding polynucleotide sequence encodes one or more antibody domains or fragments thereof.

2. The polynucleotide according to claim 1, wherein one of the encoding polynucleotide sequences encodes a light chain of an antibody or a fragment thereof.

3. The polynucleotide according to claim 2, wherein the light chain or a fragment thereof is encoded by a variable domain encoding polynucleotide sequence and a constant domain encoding polynucleotide sequences.

4. The polynucleotide according to claim 1, wherein one of the encoding polynucleotide sequences encodes a heavy chain of an antibody or a fragment thereof.

5. The polynucleotide according to claim 4, wherein the heavy chain or a fragment thereof is encoded by a variable domain encoding polynucleotide sequence and one or more constant domain encoding polynucleotide sequences.

6. The polynucleotide according to claim 1, wherein the polynucleotide comprises two different promoter sequences.

7. A cell comprising a transcriptionally active recombinant linear polynucleotide as defined in claim 1.

8. An expression system comprising a polynucleotide as defined in claim 1 and a solvent or medium.

9. The expression system according to claim 8, wherein the expression system further comprises a host cell.

10. A method of producing a transcriptionally active recombinant linear polynucleotide encoding a multimeric protein comprising in the following order, a first promoter sequence, a first encoding polynucleotide sequence, a bidirectional polyadenylation sequence, a second encoding polynucleotide sequence and a second promoter sequence, wherein the first and second encoding polynucleotide sequences are in convergent transcriptional orientation, each encoding polynucleotide sequence encodes a component of the multimeric protein, the bidirectional polyadenylation sequence is operably linked to the first and second encoding polynucleotide sequences, and the multimeric protein is an antibody or fragment thereof and each component of the multimeric protein is one or more antibody domains or fragments thereof, wherein the method comprises:

a. providing the first and second promoter sequences, the first encoding polynucleotide sequence comprising the whole or a part of a first multimeric component encoding polynucleotide sequence; the second encoding polynucleotide sequence comprising the whole or a part of a second multimeric component encoding polynucleotide sequence; and a third polynucleotide sequence comprising the bidirectional polyadenylation sequence and optionally comprising a part of the first and/or second multimeric component encoding polynucleotide sequences;
b. fusing the first encoding polynucleotide sequence to the third polynucleotide sequence;
c. fusing the second encoding polynucleotide sequence to the third polynucleotide sequence; and
d. fusing the first promoter sequence to the first encoding polynucleotide sequence and fusing the second promoter sequence to the second encoding polynucleotide sequence.

11. The method according to claim 10, wherein step b) and step c) are carried out simultaneously.

12. The method according to claim 11, wherein steps b), c) and d) are carried out simultaneously.

13. The method according to claim 10, wherein step b) and/or step c) and/or step c) are effected employing PCR.

14. The method according to claim 10, wherein the first encoding polynucleotide sequence comprises the whole first multimeric component encoding polynucleotide sequence and the second encoding polynucleotide sequence comprises the whole second multimeric component encoding polynucleotide sequence.

15. The method according to claim 10, wherein each multimeric component encoding polynucleotide sequence encodes a fusion protein of a variable domain and a constant domain and comprises a first fusion protein subunit encoding a variable domain sequence and a second fusion protein subunit encoding a constant domain sequence.

16. The method according to claim 15, wherein step a) comprises fusing the first fusion protein subunit encoding sequence and the second fusion protein subunit encoding sequence for each multimeric component encoding polynucleotide sequence.

17. The method according to claim 16, wherein the step of fusing the first fusion protein subunit encoding sequence and the second fusion protein subunit encoding sequence is carried out simultaneously with step b) and/or step c) and/or step d).

18. The method according to claim 10, wherein the first encoding polynucleotide sequence comprises a first fusion protein subunit encoding sequence, the second encoding polynucleotide sequence comprises a first fusion protein subunit encoding sequence and the third polynucleotide sequence comprising the bidirectional polyadenylation sequence further comprises a second fusion protein subunit encoding sequences at each end of the bidirectional polyadenylation sequence.

19. The method according to claim 18, wherein step a) comprises fusing the second fusion protein subunit encoding sequences to the bidirectional polyadenylation sequence thereby forming the third polynucleotide sequence.

20. The method according to claim 19, wherein the step of fusing the second fusion protein subunit encoding sequences to the bidirectional polyadenylation sequence is carried out simultaneously with step b) and/or step c) and/or step d).

21. The method according to claim 19, wherein the step of fusing the second fusion protein subunit encoding sequences to the bidirectional polyadenylation sequence is effected employing PCR.

22. The method to claim 10, wherein one of the encoding polynucleotide sequences encodes a light chain of an antibody or a fragment thereof.

23. A method for obtaining a recombinant antibody with a desired function, comprising:
(a) providing a population of antibody-forming cells suspected of containing at least one cell capable of producing an antibody exhibiting the desired function;
(b) generating a transcriptionally active recombinant linear polynucleotide from the antibody forming cells obtained in step (a) wherein the transcriptionally active recombinant linear polynucleotide comprises in the following order:
  (i) a first promoter sequence;
  (ii) a first encoding polynucleotide sequence encoding one or more antibody variable domains or fragments thereof of an antibody produced by an antibody-forming cell obtained in step (a);
  (iii) a bidirectional polyadenylation sequence
  (iv) a second encoding polynucleotide sequence encoding one or more antibody variable domains or fragments thereof of an antibody produced by an antibody-forming cell obtained in step (a); and
  (v) a second promoter sequence,
    wherein the first and second encoding polynucleotide sequences are in convergent transcriptional orientation, each encoding polynucleotide sequence encodes a component of an antibody and the bidirectional polyadenylation sequence is operably linked to the first and second encoding polynucleotide sequences;
(c) expressing a recombinant antibody using the transcriptionally active recombinant linear polynucleotide generated in step (b);
(d) screening the recombinant antibody produced by step (c) for the desired function; and
(e) optionally repeating steps (b), (c) and (d) to identify a recombinant antibody exhibiting the desired function.

24. The method according to claim 23, wherein the method comprises a first screening step prior to step (b) in which the population of antibody-forming cells provided in step (a) are screened to identify an antibody-forming cell or a population of antibody-forming cells producing an antibody exhibiting the desired function, and in step (b) the transcriptionally active recombinant linear polynucleotide is generated from the cell or population of cells identified by the first screening step.

25. The method according to claim 24, wherein the method further comprises an isolating step prior to step (b) of isolating a single antibody-forming cell producing an antibody exhibiting the desired function from a population of antibody-forming cells identified by the first screening step and in step (b) the transcriptionally active recombinant linear polynucleotide is generated from the single isolated antibody-forming cell.

26. The method according to claim 25, wherein the first screening step and the isolating step are carried out simultaneously.

27. The method according to claim 24, wherein prior to step (b) the method comprises an isolating step of directly isolating a single antibody-forming cell from the population of antibody-forming cells obtained in step (a) without first screening the population of antibody-forming cells provided in step (a) for an antibody-forming cell producing an antibody exhibiting the desired function and in step (b) the transcriptionally active recombinant linear polynucleotide is generated from the single isolated antibody-forming cell.

28. The method according to claim 23, wherein the antibody-forming cells produce antibodies comprising a heavy chain and a light chain.

29. The method according to claim 28, wherein the recombinant antibody expressed in step (c) retains the original light chain and heavy chain pairing of an antibody produced by an antibody-forming cell.

30. The method according to claim 28, wherein step (b) comprises generating a transcriptionally active recombinant linear polynucleotide wherein the first encoding polynucleotide sequence encodes a light chain or a fragment thereof and the second encoding polynucleotide sequence encodes a heavy chain or a fragment thereof for each recombinant antibody.

31. The method according to claim 28, wherein the light chain or a fragment thereof is encoded by a variable domain encoding polynucleotide sequence and a constant domain encoding polynucleotide sequence and the heavy chain or a fragment thereof is encoded by a variable domain encoding polynucleotide sequence and one or more constant domain encoding polynucleotide sequences.

32. The method according to claim 23, wherein step (d) comprises screening to detect binding of the recombinant antibody to a selected antigen.

33. The method according to claim 23, wherein step (c) comprises transfecting the transcriptionally active recombinant linear polynucleotide into a host cell; and growing said host cells in an appropriate medium.

34. The method according to claim 23, wherein step (c) comprises expressing the antibody from the transcriptionally active recombinant linear polynucleotide in a cell-free expression system.

35. The method according to claim 23, wherein step (b) comprises the method of as defined in claim 10.

36. A method of expressing a multimeric protein, comprising:
a) transfecting a cell with the transcriptionally active recombinant linear polynucleotide as defined in claim 1; and
b) expressing the multimeric protein encoded by the transcriptionally active recombinant linear polynucleotide.

37. A transcriptionally active recombinant linear polynucleotide encoding an antibody or fragment thereof, comprising in the following order:

(a) a first promoter sequence, which is operably linked to
(b) a first encoding polynucleotide that encodes one or more domains of the antibody or fragments thereof, which is operably linked to
(c) a bidirectional polyadenylation sequence that is capable of forming the end of each RNA transcript formed, which is operably linked to
(d) a second encoding polynucleotide sequence that encodes one or more domains of the antibody or fragments thereof, which is operably linked to
(e) a second promoter sequence,
wherein the first polynucleotide of (b) and the second polynucleotide of (d) are in convergent transcriptional orientation.

* * * * *